(12) United States Patent
Ni et al.

(10) Patent No.: US 12,152,571 B2
(45) Date of Patent: Nov. 26, 2024

(54) DISTANCE ADJUSTMENT APPARATUS AND CONTROL METHOD OF DISTANCE ADJUSTMENT APPARATUS

(71) Applicant: Huawei Technologies Co., Ltd., Shenzhen (CN)

(72) Inventors: Gang Ni, Nanjing (CN); Yufei Sun, Shanghai (CN); Huimin Zhang, Shanghai (CN); Jenhui Liao, Shanghai (CN); Dexin Xu, Shenzhen (CN); Xuhai Zhang, Nanjing (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 18/264,825

(22) PCT Filed: Jan. 21, 2022

(86) PCT No.: PCT/CN2022/073247
§ 371 (c)(1),
(2) Date: Aug. 9, 2023

(87) PCT Pub. No.: WO2022/170942
PCT Pub. Date: Aug. 18, 2022

(65) Prior Publication Data
US 2024/0117796 A1     Apr. 11, 2024

(30) Foreign Application Priority Data

Feb. 10, 2021 (CN) .......................... 202110185526.1
Aug. 6, 2021 (CN) .......................... 202110900779.2

(51) Int. Cl.
*F03G 7/06* (2006.01)
*A61B 5/00* (2006.01)
(Continued)

(52) U.S. Cl.
CPC ............ *F03G 7/064* (2021.08); *A61B 5/6803* (2013.01); *A61B 5/6843* (2013.01);
(Continued)

(58) Field of Classification Search
CPC .. F03G 7/064; F03G 7/06145; F03G 7/06143; F03G 7/0665; A61B 5/6803;
(Continued)

(56) References Cited

U.S. PATENT DOCUMENTS 10,805,718 B1 * 10/2020 Porter ..................... F16F 1/021
2013/0015376 A1 * 1/2013 Kocurek ............. E21B 41/0007
60/527

(Continued)

*Primary Examiner* — Hoang M Nguyen
(74) *Attorney, Agent, or Firm* — Slater Matsil, LLP

(57) ABSTRACT

A distance adjustment apparatus and a control method of the distance adjustment apparatus are provided. The distance adjustment apparatus includes a connection component, and the connection component includes a first component and a second component. The first component is connected to the second component, and a memory alloy component is disposed in a connection region between the first component and the second component. The memory alloy component is controlled by a current to drive the first component and the second component to move closer to and/or away from each other.

20 Claims, 13 Drawing Sheets

(51) Int. Cl.
 *G02B 7/02* (2021.01)
 *G02B 27/01* (2006.01)
 *G02C 5/20* (2006.01)
 *G02C 5/22* (2006.01)
 *H04R 1/10* (2006.01)

(52) U.S. Cl.
 CPC ........... *F03G 7/06145* (2021.08); *G02B 7/02* (2013.01); *G02B 27/0176* (2013.01); *G02C 5/20* (2013.01); *G02C 5/22* (2013.01); *H04R 1/1008* (2013.01); *H04R 1/1066* (2013.01); *F03G 7/06143* (2021.08); *F03G 7/0665* (2021.08); *G02B 2027/0178* (2013.01)

(58) Field of Classification Search
 CPC .... A61B 5/6843; G02B 7/02; G02B 27/0176; G02B 2027/0178; G02C 5/20; G02C 5/22; H04R 1/1008; H04R 1/1066
 USPC ................................................... 60/527–529
 See application file for complete search history.

(56) References Cited

U.S. PATENT DOCUMENTS

| | | | |
|---|---|---|---|
| 2019/0302396 A1* | 10/2019 | Zhu | H02N 10/00 |
| 2020/0379208 A1* | 12/2020 | Li | G02B 7/09 |
| 2022/0095029 A1* | 3/2022 | Zheng | H04R 1/1091 |
| 2022/0236566 A1* | 7/2022 | Kim | G03B 17/17 |

\* cited by examiner

DISTANCE ADJUSTMENT APPARATUS AND CONTROL METHOD OF DISTANCE ADJUSTMENT APPARATUS

CROSS-REFERENCE TO RELATED APPLICATIONS

This application is a national stage of International Application No. PCT/CN2022/073247, filed on Jan. 21, 2022, which claims priority to Chinese Patent Application No. 202110185526.1, filed on Feb. 10, 2021 and Chinese Patent Application No. 202110900779.2, filed on Aug. 6, 2021. All of the aforementioned patent applications are hereby incorporated by reference in their entireties.

TECHNICAL FIELD

This application relates to the field of terminal device technologies, and is specifically a distance adjustment apparatus and a control method of the distance adjustment apparatus.

BACKGROUND

A wearable device usually refers to a micro electronic device that can be worn on a body to perform an activity, and may be used independently, or may be used as a portable accessory of a mobile terminal. Some wearable devices may be worn by using fastening belts. For example, a headset may be worn on the head of a user by using a connection component, and a smart watch or band may be worn on a wrist of a user by using a connection component. In a wearing process of the wearable device, to ensure wearing comfort of the user, a specific gap needs to be reserved between the connection component and the user. Due to individual differences of users, adaptively adjusting wearing comfort is an important method for improving user experience of the wearable device.

For example, how a user can wear a headset on the head of the user comfortably, how a smart watch or band can adaptively adjust tightness based on thickness of a wrist of a user, and how AR/VR glasses can adjust a distance between arms or frames based on a distance between the head or eyes of a wearer user and the AR/VR glasses are urgent problems to be resolved. An existing wearable device is usually manually adjusted, and cannot be adaptively and steplessly adjusted.

In addition, a sensor configured to detect a heart rate or blood pressure of a user is usually disposed in a current smart watch or band product, and such a sensor is usually disposed at a rear cover position of the smart watch or band product. During heart rate or blood pressure detection, the sensor needs to be close to a wrist of the user to improve detection precision. However, because there is a gap between a connection component and the wrist of the user, a compactness degree of the sensor and the wrist is reduced. As a result, the detection precision of the smart watch or band product is reduced. In addition, several types of fastening belts of the foregoing structure are inconvenient during length adjustment. If a method of manually tightening the fastening belt in a detection process to improve the compactness degree of the sensor is adopted, the detection process is complicated, use convenience of a terminal device product is reduced, and user experience is degraded.

SUMMARY

This application provides a distance adjustment apparatus and a control method of the distance adjustment apparatus, so that a length of a connection component can be electrically and steplessly adjusted.

According to a first aspect, this application provides a distance adjustment apparatus. The distance adjustment apparatus includes a first component and a second component, the first component is connected to the second component, a memory alloy component is disposed in a connection region between the first component and the second component, and the memory alloy component is controlled by a current to drive the first component and the second component to move closer to and/or away from each other.

In a specific technical solution, the memory alloy component includes a first memory alloy component and a second memory alloy component. One end of the first memory alloy component is fastened to the first component, and the other end drives the second component to move in a first direction relative to the first component; when a temperature of the first memory alloy component is lower than a set threshold, the first memory alloy component is in a first form; and when the temperature of the first memory alloy component is higher than the set threshold, the first memory alloy component is in a second form, and the first memory alloy component is connected to two electrodes, where the first memory alloy component can be controlled by the current to change between the first form and the second form, to drive the second component to move in the first direction relative to the first component. One end of the second memory alloy component is fastened to the first component, the other end drives the second component to move in a second direction relative to the first component, and the first direction is opposite to the second direction; when a temperature of the second memory alloy component is lower than a set threshold, the second memory alloy component is in the second form; and when the temperature of the second memory alloy component is higher than the set threshold, the second memory alloy component is in the first form, and the second memory alloy component is connected to two electrodes. The second memory alloy component of a second driving part can be controlled by the current to change between the first form and the second form, to drive the second component to move in the second direction relative to the first component.

When the distance adjustment apparatus is specifically disposed, the distance adjustment apparatus further includes an elastic material layer that is stacked and fastened and that one-to-one corresponds to the first memory alloy component; and an elastic material layer that is stacked and fastened and that one-to-one corresponds to the second memory alloy component.

In a specific technical solution, the memory alloy component includes a plurality of first memory alloy components and a plurality of second memory alloy components.

The first memory alloy component and the second memory alloy component may be located on a same side of the second component. Alternatively, the second component is located between the first memory alloy component and the second memory alloy component. In other words, the first memory alloy component and the second memory alloy component are located on two sides of the second component.

The distance adjustment apparatus may further include an auxiliary part. The auxiliary part is disposed between the second component and the first component, when the auxiliary part is in a first status, the first memory alloy component or the second memory alloy component can be in contact with the second component, and when the auxiliary part is in a second status, there is a gap between the first memory alloy component or the second memory alloy component, and the second component. The first memory alloy component and the second memory alloy component are bent in the first form in the second direction, and are bent in the second form in the first direction. The first memory alloy component changes from the first form to the second form, to drive the second component to move in the first direction. The second memory alloy component changes from the second form to the first form, to drive the second component to move in the second direction.

When the auxiliary part is specifically disposed, one end of the auxiliary part is fastened to the first component, and the other end faces the second component; the first memory alloy component and the second memory alloy component are disposed between the first component and the second component; and when the auxiliary part is in the second status, the second component is driven to move in a direction away from a surface of the first component, and there is a gap between the second component, and the first memory alloy component and the second memory alloy component.

When the second component is located between the first memory alloy component and the second memory alloy component, one end of the auxiliary part is fastened to the first component, the other end faces the second component, the auxiliary part includes a first auxiliary part and a second auxiliary part, the first auxiliary part and a first driving part are on a same side, and the second auxiliary part and the second driving part are on a same side. When the first auxiliary part is in the second status, the second component is driven to move in a direction away from the first driving part, and there is a gap between the first driving part and the second component. When the second auxiliary part is in the second status, the second component is driven to move in a direction away from the second driving part, and there is the gap between the first driving part and the second component.

When a structure of the auxiliary part is specifically disposed, the auxiliary part may include a first memory alloy spring, and the first memory alloy spring is connected to two electrodes; when a temperature of the first memory alloy spring is lower than a set threshold, the first memory alloy spring is of a first length; and when the temperature of the first memory alloy spring is higher than the set threshold, the first memory alloy spring extends towards the second component to a second length, where the second length is greater than the first length, and the second component is driven to move in the direction away from the surface of the first component.

In addition, the auxiliary part further includes a first return spring, the first return spring is disposed in parallel with the first memory alloy spring, when the first memory alloy spring is of the first length, the first return spring is in an energy release state, and when the first memory alloy spring is of the second length, the first return spring is in an energy storage state.

When the memory alloy component is specifically disposed, the first memory alloy component has an elastic layer facing an end of the second component, and the second memory alloy component has an elastic layer facing an end of the second component.

In another technical solution, the first memory alloy component and the second memory alloy component are bent in the first form parallel to the first direction, and are bent in the second form in a direction away from the second component. The first memory alloy component includes a first end and a second end that are distributed in the second direction, the first end is fastened to the first component, and the second end is connected to a first linkage rod; the first linkage rod includes a third end and a fourth end that are distributed in the second direction, and the second end is rotatably connected to the fourth end; and a first baffle is fastened to the second end, the first memory alloy component changes from the second form to the first form, the fourth end abuts against the first baffle, and the third end drives the second component to move in the first direction. The second memory alloy component includes a fifth end and a sixth end that are distributed in the second direction, the sixth end is fastened to the first component, and the fifth end is connected to a second linkage rod; the second linkage rod includes a seventh end and an eighth end that are distributed in the second direction, and the fifth end is rotatably connected to the seventh end; and a second baffle is fastened to the fifth end, the second memory alloy component changes from the second form to the first form, the seventh end abuts against the second baffle, and the eighth end drives the second component to move in the second direction.

To improve friction between the first linkage rod and the second component, and improve friction between the second linkage rod and the second component, the third end of the first linkage rod has an elastic layer, and the eighth end of the second linkage rod has an elastic layer.

The distance adjustment apparatus further includes a stop structure. The stop structure is disposed between the second component and the first component, when the stop structure is in the first status, the second component can move closer to the first component, and when the stop structure is in the second status, the stop structure is fixedly connected to the second component and the first component.

When the stop structure is specifically disposed, the stop structure includes a rack, a gear, a clamping member, an elastic member, and a memory alloy structure, where the gear is adapted to the rack, and the clamping member can be engaged with the gear. The rack is fixedly disposed in the first component, a rotating shaft of the gear is fixedly disposed in the second component, the elastic member is disposed between the clamping member and the second component, and the memory alloy structure is connected between the clamping member and the second component; or the rack is fixedly disposed in the second component, the rotating shaft of the gear is fixedly disposed in the first component, the elastic member is disposed between the clamping member and the first component, and the memory alloy structure is connected between the clamping member and the first component. When a temperature of the memory alloy structure is lower than a set threshold, the memory alloy structure is in the first form, and the elastic member drives the clamping member to engage with the gear; and when the temperature of the memory alloy structure is higher than the set threshold, the memory alloy structure is in the second form, the clamping member is driven to move away from the gear, the gear can move in mesh with the rack, and the elastic member is in the energy storage state.

In another technical solution, the distance adjustment apparatus further includes a second return spring and a stop structure, where the memory alloy component is a second memory alloy spring. One end of the second memory alloy spring is connected to the first component, the other end is connected to the second component, and the second memory alloy spring is connected to two electrodes; when a temperature of the second memory alloy spring is lower than a set threshold, the second memory alloy spring is of a first length; and when the temperature of the second memory alloy spring is higher than the set threshold, the second memory alloy spring telescopically deforms in a first direction to a second length, where the second length is different from the first length, and the second component is driven to move in the first direction relative to the first component. One end of the second return spring is connected to the first component, and the other end is connected to the second component; and when the second memory alloy spring is of the second length, the second return spring can drive the second component to move in a second direction relative to the first component, where the first direction is opposite to the second direction. The stop structure is disposed between the second component and the first component; when the stop structure is in a first status, the second component can move closer to the first component; and when the stop structure is in a second status, the stop structure is fixedly connected to the second component and the first component.

A specific material of the second return spring is not limited, and may be a common spring. Alternatively, the second return spring may further be a second return spring made of a memory alloy material.

When the distance adjustment apparatus is specifically disposed, the distance adjustment apparatus further includes a first guide member, where the first guide member extends in the first direction, and the second return spring and the second memory alloy spring are mounted to the first guide member. In this way, stability of movement of the second return spring and the second memory alloy spring is improved.

A total quantity of second memory alloy springs and second return springs included in the distance adjustment apparatus is at least three.

In a specific technical solution, the second memory alloy springs and the second return springs are spaced one by one; or the second memory alloy springs are symmetrically arranged about a symmetry axis of the second component, the second return springs are symmetrically arranged about the symmetry axis of the second component, and the symmetry axis extends in the first direction.

The stop structure specifically includes a rack, a gear, a clamping member, an elastic member, and a memory alloy structure, where the gear is adapted to the rack, and the clamping member can be engaged with the gear. The rack is fixedly disposed in the first component, a rotating shaft of the gear is fixedly disposed in the second component, the elastic member is disposed between the clamping member and the second component, and the memory alloy structure is connected between the clamping member and the second component; or the rack is fixedly disposed in the second component, the rotating shaft of the gear is fixedly disposed in the first component, the elastic member is disposed between the clamping member and the first component, and the memory alloy structure is connected between the clamping member and the first component. When a temperature of the memory alloy structure is lower than a set threshold, the memory alloy structure is in a first form, and the elastic member drives the clamping member to engage with the gear; and when the temperature of the memory alloy structure is higher than the set threshold, the memory alloy structure is in a second form, the clamping member is driven to move away from the gear, the gear can move in mesh with the rack, and the elastic member is in an energy storage state.

The distance adjustment apparatus includes a wearable device; a first sensor, a power supply module, and a controller are disposed in the wearable device; the first sensor is disposed in the wearable device, and is configured to detect a pressure value between the wearable device and a user; the power supply module is connected to the memory alloy component, and is configured to drive the memory alloy component to deform; and the controller is connected to the power supply module and the first sensor, and is configured to: control, based on the pressure value detected by the first sensor, a current input by the power supply module to the memory alloy component, and drive the first component and the second component to move closer to or away from each other.

A specific type of the first sensor is not limited, and may include a force sensor and a distance sensor. The distance sensor may include a capacitive proximity sensor, an ultrasonic distance sensor, a laser ranging sensor, an infrared ranging sensor, and a light sensing sensor. In conclusion, the first sensor may obtain a position relationship between the wearable device and a human body, so that the controller may control, based on the position relationship, the first component and the second component to move closer to or away from each other.

In a specific technical solution, the distance adjustment apparatus includes at least two first sensors, so that accuracy of detecting a position relationship between the distance adjustment apparatus and the user can be improved.

When the distance adjustment apparatus includes the at least two first sensors, the distance adjustment apparatus may include at least two types of first sensor, for example, may include the force sensor and the distance sensor, so that the force sensor and the distance sensor may be sequentially spaced.

A second sensor is further disposed in the wearable device; the second sensor is connected to the controller; the second sensor is configured to send a use state signal to the controller when the wearable device is in a use state; and the controller is configured to: after receiving the use state signal, control the current input by the power supply module to the memory alloy component.

In another technical solution, the distance adjustment apparatus includes a wearable device; a power supply module and a voice controller are disposed in the wearable device; the power supply module is connected to the memory alloy component, and is configured to drive the memory alloy component to deform; and the voice controller and the power supply module are configured to: receive a voice instruction of a user, and control, according to the voice instruction, a current input by the power supply module to the memory alloy component, to drive the first component and the second component to move closer to or away from each other.

According to a second aspect, this application further provides a control method of the distance adjustment apparatus. The control method includes: obtaining a position relationship signal between the wearable device and the user; and determining whether the position relationship signal is within a set range, if yes, controlling the memory alloy component to stop working, and if no, controlling the memory alloy component to drive the first component and the second component to move closer to or away from each other. In this solution, a length of the wearable device may be adjusted based on the position relationship between the wearable device and the user, so that the user can wear the wearable device comfortably.

In a specific technical solution, the position relationship signal includes a pressure value or a distance value, or includes both a pressure value and a distance value.

When the position information includes both the pressure value and the distance value, the control method may specifically include: first obtaining a distance value between the wearable device and the user; determining whether the distance value is within a first set range, if yes, controlling the memory alloy component to stop working, and if no, controlling the memory alloy component to drive the first component and the second component to move closer to or away from each other.

After the controlling the memory alloy component to stop working, the method includes: obtaining a pressure value between the wearable device and the user; and determining whether the pressure value is within a second set range, if yes, controlling the memory alloy component to stop working, and if no, controlling the memory alloy component to drive the first component and the second component to move closer to or away from each other. In this solution, a distance between the wearable device and the user is first adjusted by using the distance value, and it is further determined, based on the pressure value between the wearable device and the user, whether the user wears the wearable device comfortably.

In addition, in the foregoing control method, before the obtaining a position relationship signal between the wearable device and the user, the method includes: obtaining a use state signal of the wearable device. To be specific, only when the wearable device is in a use state, the position relationship between the wearable device and the user is obtained, and the memory alloy component is further controlled to drive the first component and the second component to move or stop working.

The foregoing control method further includes: forming user information through self-learning, and controlling, based on the user information, the memory alloy component to drive the first component and the second component to set positions. After the user wears the wearable device for a plurality of times for a long time, in the control method, a position relationship between the first component and the second component may be obtained when the user wears the wearable device comfortably, and the position relationship is used as the set positions. In the control method, when the user wears the wearable device, the first component and the second component may be directly adjusted to the set positions. In this solution, an adjustment speed of adjusting the wearable device can be increased.

REFERENCE NUMERALS

Figure 1:
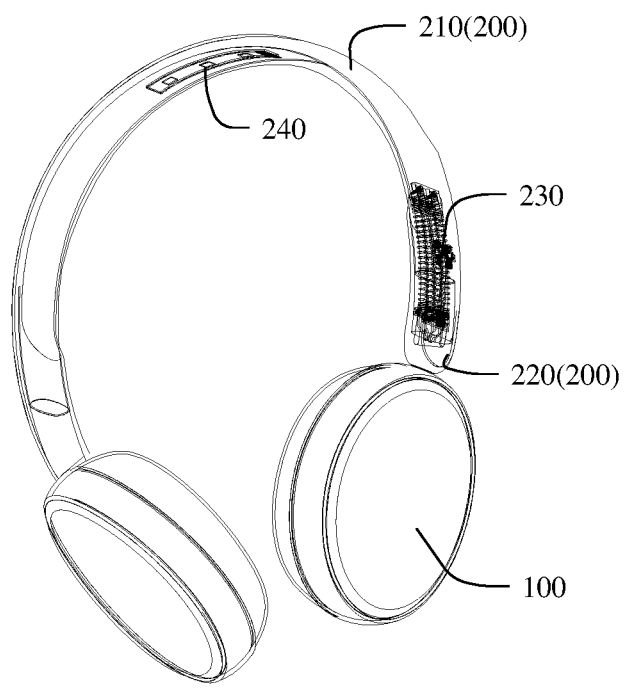
FIG. 1 is a schematic diagram of a structure of a distance adjustment apparatus according to an embodiment of this application.

100: device body; 200: connection component;
210: first connection component; 220: second connection component;
230: distance adjustment apparatus; 240: first sensor;
250: power supply module; 260: controller;
270: convex arc surface; 280: plane;
1: first component; 2: second component;
3: memory alloy component; 31: elastic material layer;
4: first driving part; 41: first memory alloy component;
411: first end; 412: second end;
42: first linkage rod; 421: third end;
422: fourth end; 43: first baffle;
44: second memory alloy spring; 5: second driving part;
51: second memory alloy component; 511: fifth end;
512: sixth end; 52: second linkage rod;
521: seventh end; 522: eighth end;
53: second baffle; 54: second return spring;
6: auxiliary part; 61: first memory alloy spring;
62: first return spring; 7: elastic layer;
8: stop structure; 81: gear;

811: rotating shaft; 82: rack;
83: clamping member; 84: elastic member;
85: memory alloy structure; and 9: first guide member.

DETAILED DESCRIPTION OF ILLUSTRATIVE EMBODIMENTS

Terms used in the following embodiments are merely intended to describe particular embodiments, but are not intended to limit this application. Terms "one", "a" and "this" of singular forms used in this specification and the appended claims of this application are also intended to include expressions such as "one or more", unless otherwise specified in the context clearly.

Reference to "an embodiment", "specific embodiments", or the like described in this specification means that one or more embodiments of this application include a specific feature, structure, or characteristic described with reference to the embodiments. Terms "include", "comprise", "have", and their variants all mean "include but are not limited to", unless otherwise specifically emphasized.

To facilitate understanding of a distance adjustment apparatus and a control method of the distance adjustment apparatus provided in embodiments of this application, the following first describes an application scenario of the distance adjustment apparatus. The distance adjustment apparatus may be a terminal device or a module component. The terminal device may be any terminal device, especially a wearable device, that needs to adjust a length of a partial structure. The terminal device may include a device body and a connection component, and a use state of the entire terminal device may be adjusted by adjusting a length of the connection component. The wearable device is used as an example. A user needs to adjust a length of a connection component, so that the user can wear the wearable device comfortably. Especially when the wearable device has a sensor for detection, the sensor may be in contact with the user at proper pressure. In a conventional technology, a length of a connection component is usually manually adjusted. On one hand, a plurality of connection components cannot implement stepless length adjustment, and therefore it is difficult to make a user comfortable. On the other hand, manual adjustment is cumbersome and sometimes inconvenient. Therefore, this application provides the distance adjustment apparatus and the control method of the distance adjustment apparatus, so that the length of the connection component can be electrically and steplessly adjusted.

Figure 2:
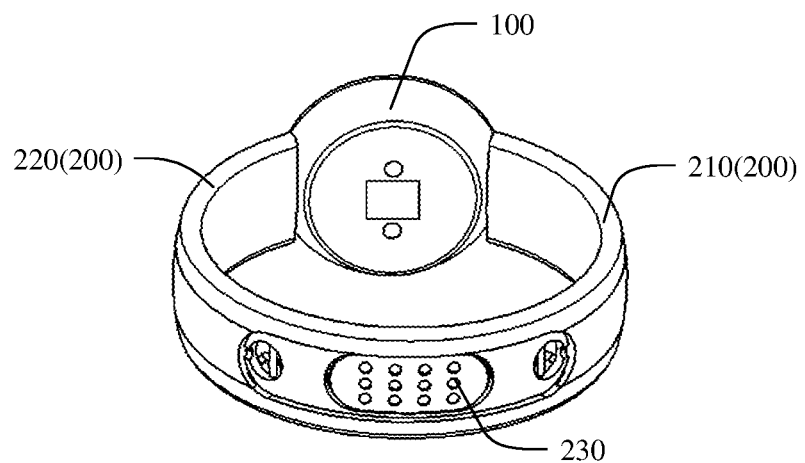
FIG. 2 is a schematic diagram of another structure of a distance adjustment apparatus according to an embodiment of this application.

FIG. 1 is a schematic diagram of a structure of a distance adjustment apparatus according to an embodiment of this application, and FIG. 2 is a schematic diagram of another structure of a distance adjustment apparatus according to an embodiment of this application. As shown in FIG. 1 and FIG. 2, the distance adjustment apparatus includes a device body 100 and a connection component 200 connected to the device body 100. The connection component 200 includes a first connection component 210, a second connection component 220, and a memory alloy component 3. The memory alloy component 3 is disposed between the first connection component 210 and the second connection component 220, and can drive the first connection component 210 and the second connection component 220 to move closer to and/or away from each other, thereby adjusting a length of the connection component 200.

The distance adjustment apparatus may be a wearable device, for example, a headset, a watch, a band, or AR/VR glasses, or may be an apparatus that needs to adjust a distance, for example, a belt, a shoelace, a detection device, or a display stand. A specific type is not limited in this application. When the wearable device is the headset, as shown in FIG. 1, it may be considered that two headset parts of the headset are the device body 100, and a head beam connected to the two headset parts is the connection component 200. When the wearable device is the watch, as shown in FIG. 2, it may be considered that a watch face of the watch is the device body 100, and a watchband is the connection component 200. In conclusion, a main functional component of the distance adjustment apparatus is the device body 100, and the connection component 200 mainly functions as a connection. The length of the connection component 200 is adjusted by using the memory alloy component 3, so that a position of the device body 100 may be adjusted. Alternatively, when the distance adjustment apparatus is the wearable device, a pressure value, that is, comfort, between the wearable device and a user may be adjusted. Alternatively, when the distance adjustment apparatus is the detection device, a pressure value between the detection device and a user may be adjusted, which helps improve detection precision of the detection device.

It should be noted that the first connection component 210 and the second connection component 220 in this embodiment of this application may be in a split structure, or may be connected using a soft material, in other words, the first connection component 210 and the second connection component 220 are connected to form an integrated structure. Alternatively, the first connection component 210 and the second connection component 220 are two independent parts, which are applicable to technical solutions of this application.

Figure 3:
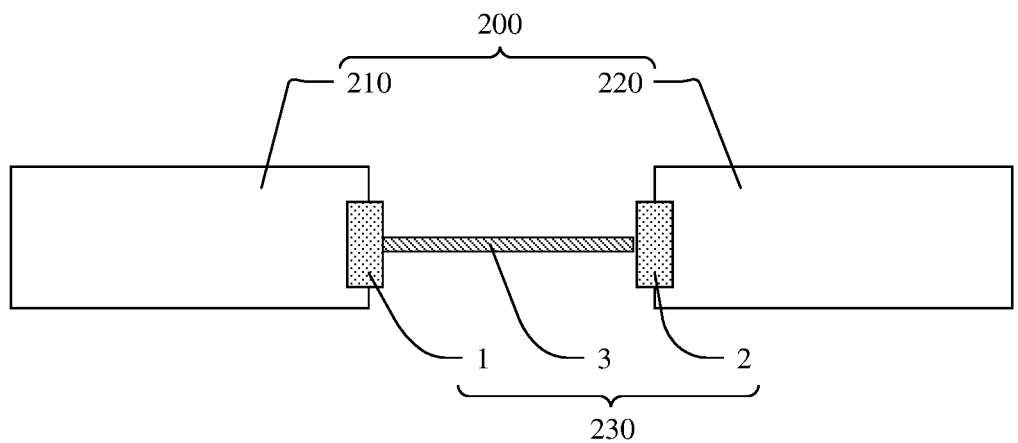
FIG. 3 is a schematic diagram of a partial structure of a distance adjustment apparatus according to an embodiment of this application.

FIG. 3 is a schematic diagram of a structure of a distance adjustment apparatus according to an embodiment of this application. Refer to FIG. 3. The distance adjustment apparatus 230 specifically includes a first component 1, a second component 2, and the memory alloy component 3. The memory alloy component 3 can conduct electricity, and a current may cause a temperature of the memory alloy component 3 to rise. Specifically, when the temperature of the memory alloy component 3 is lower than a set threshold, the memory alloy component 3 is in a first form, and when the temperature of the memory alloy component 3 is higher than the set threshold, the memory alloy component 3 is in a second form. The temperature of the memory alloy component 3 may be controlled by controlling a value or on/off of the current, so that a form of the memory alloy component 3 may change. The memory alloy component 3 is connected between the first component 1 and the second component 2, and when the form of the memory alloy component 3 changes, the first component 1 and the second component 2 may be driven to move closer to and/or away from each other. The first component 1 and the first connection component 210 are fixedly disposed, and the second component 2 and the second connection component 220 are fixedly disposed. Alternatively, the first component 1 is equivalent to the first connection component 210, and the second component 2 is equivalent to the second connection component 220. This is not limited in this application. Therefore, when the form of the memory alloy component 3 changes, the first connection component 210 and the second connection component 220 can be driven to move closer to and/or away from each other. It may be understood that, when the first connection component 210 and the second connection component 220 move closer to each other, the overall length of the connection component 200 becomes shorter. When the first connection component 210 and the second connection component 220 move away from each other, the overall length of the connection component 200 becomes longer. In this solution, the memory alloy component 3 may be driven by controlling the current, to adjust the length of the connection component 200 of the distance adjustment apparatus. Operations can be simplified without manually adjusting the length of the connection component 200 in a push-pull manner or the like. In addition, in the solution, the memory alloy component 3 may be further used to implement stepless adjustment, which is beneficial to improving user experience and comfort.

Figure 4:
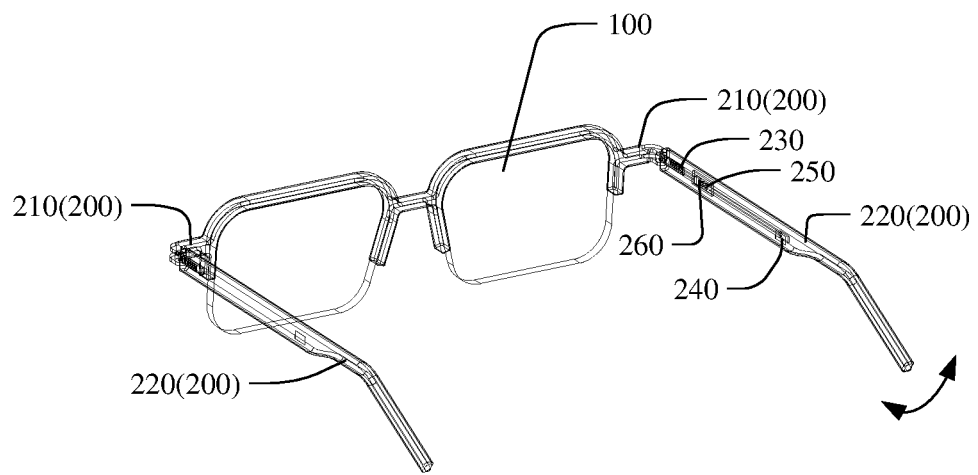
FIG. 4 is a schematic diagram of another structure of a distance adjustment apparatus according to an embodiment of this application.

FIG. 4 is another schematic diagram of a structure of a distance adjustment apparatus according to an embodiment of this application. Refer to FIG. 2 and FIG. 4. The distance adjustment apparatus may further include a first sensor 240, a power supply module 250, and a controller 260. The first sensor 240 is disposed in the distance adjustment apparatus. Specifically, a specific position of the first sensor 240 in the distance adjustment apparatus may be designed based on an actual product requirement. For example, the distance adjustment apparatus is a headset, and the first sensor 240 may be disposed in a head beam, that is, the connection component 200, to monitor a pressure value between the head beam and the head of a user, so that the user wears the headset comfortably. When the distance adjustment apparatus is a watch, the first sensor 240 may be disposed in a watch face or a watchband, that is, may be disposed in the device body 100, or may be disposed in the connection component 200. When the distance adjustment apparatus is a detection device, the first sensor 240 may be disposed in the device body 100, to ensure that a detection part of the detection device is well attached to a user, thereby improving detection effect.

The power supply module 250 is connected to the memory alloy component 3 of the distance adjustment apparatus 230, so that a current can be input to the memory alloy component 3 to control a temperature of the memory alloy component 3 and further control a shape change of the memory alloy component 3 between the first form and the second form. In this way, the first component 1 and the second component 2 are driven to move closer to or away from each other, so that the first connection component 210 and the second connection component 220 move closer to or away from each other. The controller 260 is connected to the power supply module 250 and the first sensor 240, and is configured to: control, based on a position relationship signal detected by the first sensor 240, the current input by the power supply module 250 to the memory alloy component 3, and drive the first connection component 210 and the second connection component 220 to move closer to or away from each other. Specifically, a proper range may be set as a set range, and the controller determines whether the position relationship signal detected by the first sensor 240 is within the set range. If yes, a status of the current connection component 200 is considered proper, and the memory alloy component 3 is controlled to stop working. If no, a status of the current connection component 200 is considered improper, and the memory alloy component 3 drives the first connection component 210 and the second connection component 220 to move closer to or away from each other until the position relationship signal detected by the first sensor 240 is within the set range.

In a specific technical solution, a type of the first sensor 240 is not limited, and may be at least one type of a force sensor, a capacitive proximity sensor, an ultrasonic distance sensor, a laser ranging sensor, an infrared ranging sensor, and a light sensing sensor. Specifically, the first sensor 240 of a proper type may be selected based on an actual situation.

Specifically, for example, the first sensor 240 is the force sensor, a position relationship is pressure between the wearable device and the user, and the position relationship signal is a pressure value. When the pressure value detected by the first sensor 240 is less than the set range, it indicates that the length of the connection component 200 is excessively large. The controller controls the distance adjustment apparatus 230 to drive the first connection component 210 and the second connection component 220 to move closer to each other, so that the length of the connection component 200 is reduced. When the pressure value detected by the first sensor 240 is greater than the set range, it indicates that the length of the connection component 200 is excessively small. The controller controls the distance adjustment apparatus 230 to drive the first connection component 210 and the second connection component 220 to move away from each other, so that the length of the connection component 200 is increased. When the pressure value detected by the first sensor 240 is within the set range, it indicates that the length of the connection component 200 is proper. The controller controls the distance adjustment apparatus 230 to stop driving the first connection component 210 and the second connection component 220 to move, so that a position relationship between the first connection component 210 and the second connection component 220 remains fixed.

The distance adjustment apparatus may be set in contact with the user. Therefore, a pressure value between the distance adjustment apparatus and the user directly affects comfort of the user for the wearable device, and directly affects detection precision for the detection device. The controller controls, based on the pressure value obtained by the first sensor 240, the current input by the power supply module to the memory alloy component 3, and further controls the distance adjustment apparatus 230 to adjust the length of the connection component 200. The distance adjustment apparatus may achieve a good working state and improve user experience. In addition, in this solution, manual adjustment of the length of the connection component 200 is not required, and an operation process is simple and intelligent.

The wearable device may include at least two first sensors to improve cooperation effect between the wearable device and the user, and improve comfort of wearing the wearable device by the user.

When the wearable device includes the at least two first sensors, specific types of the first sensors may be different. For example, the wearable device may include the force sensor and the distance sensor. When the force sensor and the distance sensor are specifically arranged, the force sensor and the distance sensor may be spaced. The wearable device may control first sensors of different types to work together, or select a first sensor of a specific type to work based on a requirement.

In addition, in another embodiment, the distance adjustment apparatus may have an operation button, and the operation button is used to control the current input by the power supply module to the memory alloy component 3, thereby controlling the distance adjustment apparatus 230 to adjust the length of the connection component 200.

Alternatively, in another embodiment, the distance adjustment apparatus may further include the power supply module and a voice controller. The power supply module is connected to the memory alloy component 3 of the distance adjustment apparatus 230, so that the current can be input to the memory alloy component 3 to control the temperature of the memory alloy component 3 and further control the shape change of the memory alloy component 3 between the first form and the second form. In this way, the first component 1 and the second component 2 are driven to move closer to or away from each other, so that the distance adjustment apparatus 230 can drive the first connection component 210 and the second connection component 220 to move closer to or away from each other. The voice controller is connected to the power supply module, and is configured to: receive a voice instruction of the user, control, according to the received voice instruction, the current input by the power supply module to the memory alloy component 3, and drive the first connection component 210 and the second connection component 220 to move closer to or away from each other. For example, the voice instruction received by the voice controller is "lengthen", and the voice controller controls the power supply module to input the current of the memory alloy component 3, to drive the first connection component 210 and the second connection component 220 to move away from each other, to lengthen the length of the connection component 200. The voice instruction received by the voice controller is "shorten", and the voice controller controls the power supply module to input the current of the memory alloy component 3, to drive the first connection component 210 and the second connection component 220 to move closer to each other, to shorten the length of the connection component 200. Specifically, specific content of the voice instruction may be set based on an actual situation.

In an embodiment, the distance adjustment apparatus further includes a second sensor. The second sensor is connected to the controller, the second sensor is configured to send a use state signal to the controller when the distance adjustment apparatus is in a use state, and the controller is configured to: after receiving the use state signal, control power of the current input by the power supply module to the memory alloy component 3. In this solution, whether the current distance adjustment apparatus is in the use state may be first determined by using the second sensor. Only when the distance adjustment apparatus is in the use state, the controller controls the distance adjustment apparatus 230 of a mobile terminal to adjust the length of the connection component 200, to improve reliability of the distance adjustment apparatus.

In a specific embodiment, a specific type of the second sensor is not limited, and may be a capacitive sensor, or may be an optical sensor, provided that whether the distance adjustment apparatus is in the use state can be detected.

FIG. 4 is a specific embodiment of a distance adjustment apparatus according to an embodiment of this application. The distance adjustment apparatus in this embodiment is glasses, the device body 100 of the distance adjustment apparatus is a lens, and the connection component 200 is a front frame and an arm. It may be considered that the front frame is the first connection component 210, and the arm is the second connection component 220. The distance adjustment apparatus 230 is disposed between the arm and the front frame, and there is a distance adjustment apparatus 230 between each arm and the front frame.

Figure 5:
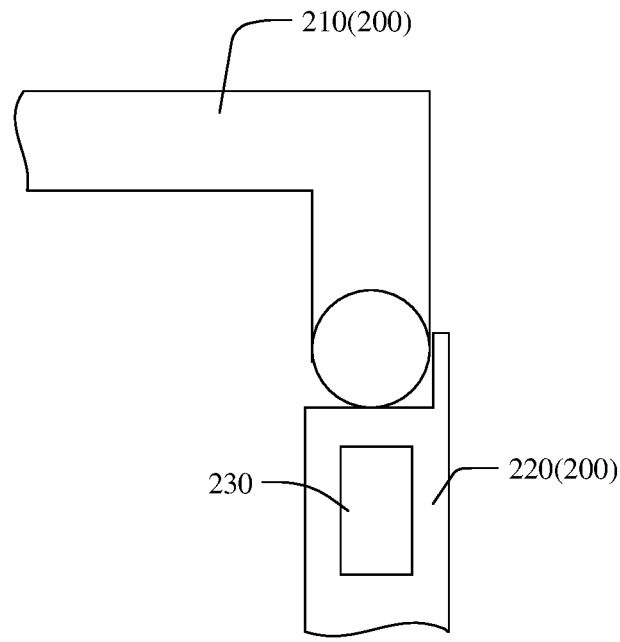
FIG. 5 is a schematic diagram of a partial structure of a distance adjustment apparatus according to a technical solution of this application.

FIG. 5 is a schematic diagram of a partial structure of a distance adjustment apparatus according to a technical solution of this application. With reference to FIG. 4 and FIG. 5, in the foregoing technical solution, a distance between two arms may be adjusted by using the distance adjustment apparatus 230. To be specific, when wearing the glasses, a user can adjust tightness between the arm and a side of a head to improve wearing experience of the user. Specifically, the first connection component 210 and the second connection component 220 are hinged, and a joint is a contact joint between a convex arc surface 270 and a plane 280. Therefore, a linear distance adjustment of the distance adjustment apparatus 230 may be converted into a swing angle adjustment. In other words, the arm and the front frame are hinged, and the joint is the contact joint between the convex arc surface 270 and the plane 280. An example in which the glasses are in a wearing state is used. When pressure between the arm and the side of the head is small, the distance adjustment apparatus may drive the arm and the front frame to move closer to each other, and the arm and the front frame rotate under action of the convex arc surface 270, so that the arm swings in a direction close to the side of the head to increase the pressure between the arm and the side of the head. When pressure between the arm and the side of the head is small, the distance adjustment apparatus may drive the arm and the front frame to move away from each other, and the arm and the front frame rotate under action of the convex arc surface 270, so that the arm swings in a direction away from the side of the head to increase the pressure between the arm and the side of the head.

Figure 6:
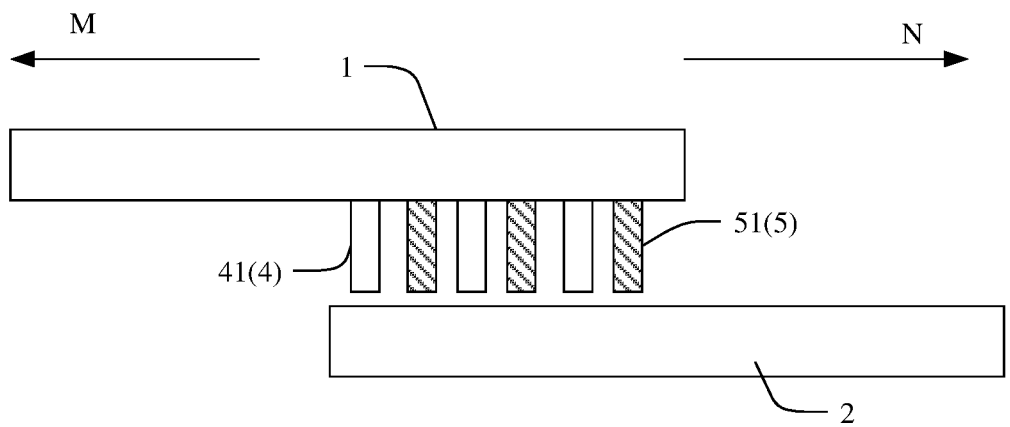
FIG. 6 is a schematic diagram of a structure of a distance adjustment apparatus according to an embodiment of this application.

The following lists several specific embodiments of structures of distance adjustment apparatuses. FIG. 6 is a schematic diagram of a structure of a distance adjustment apparatus according to an embodiment of this application. As shown in FIG. 6, the distance adjustment apparatus includes the first component 1, the second component 2, a first driving part 4, and a second driving part 5, and the second component 2 is movably mounted to the first component 1. To be specific, the second component 2 can move closer to the first component 1, and the first component 1 and the second component 2 move closer to each other or away from each other. One end of the first driving part 4 is fastened to the first component 1, and the other end can drive the second component 2 to move in a first direction relative to the first component 1. One end of the second driving part 5 is fastened to the first component 1, and the other end can drive the second component 2 to move in a second direction relative to the first component 1, where the second direction is opposite to the first direction.

Specifically, the first driving part 4 includes a first memory alloy component 41. When a temperature of the first memory alloy component 41 is lower than a set threshold, the first memory alloy component 41 is in a first form. When the temperature of the first memory alloy component 41 is higher than the set threshold, the first memory alloy component 41 is in a second form. It may be understood that a shape of the first memory alloy component 41 may vary with the temperature. To be specific, as the temperature changes to be above or below the set threshold, the first memory alloy component 41 changes from one shape to another shape. Because one end of the first memory alloy component 41 is relatively fastened to the first component 1, during deformation of the first memory alloy component 41, the other end of the first memory alloy component 41 may drive the second component 2 to move closer to the first component 1. The first memory alloy component 41 is connected to two electrodes, and the first memory alloy component 41 may be connected to a circuit by using the two electrodes. In other words, a current may be input to the first memory alloy component 41, and the current causes the temperature of the first memory alloy component 41 to change. Further, the first memory alloy component 41 may be controlled to be in a first form or a second form by controlling a value or on/off of the current, and the first memory alloy component 41 may change between the first form and the second form to drive the second component 2 to move in the first direction relative to the first component 1.

The second driving part 5 is similar to the first driving part 4. One end of the second driving part 5 is fastened to the first component 1, and the other end of the second driving part 5 drives the second component 2 to move in the second direction relative to the first component 1, where the first direction is opposite to the second direction. In other words, the first driving part 4 and the second driving part 5 separately drive the second component 2 to move in opposite directions closer to the first component 1. The second driving part 5 also includes a second memory alloy component 51. When a temperature of the second memory alloy component 51 is lower than a set threshold, the second memory alloy component 51 is in the second form; and when the temperature of the second memory alloy component 51 is higher than the set threshold, the second memory alloy component 51 is in the first form. The second memory alloy component 51 is connected to two electrodes, and the second memory alloy component 51 of the second driving part 5 can change between the first form and the second form, to drive the second component 2 to move in the second direction relative to the first component 1. The second memory alloy component 51 is similar to the first memory alloy component 41. Details are not described herein again.

In the technical solution of this application, the memory alloy component 3 is applied to the distance adjustment apparatus by utilizing features that the memory alloy component 3 can conduct electricity and the memory alloy component 3 can change the form after the current affects the temperature of the memory alloy component 3, to drive the second component 2 to move closer to the first component 1 through the deformation of the memory alloy component 3. Specifically, in the foregoing technical solution, the distance adjustment apparatus includes the first driving part 4 and the second driving part 5, so that the second component 2 may be separately driven to move in two opposite directions of the first direction and the second direction relative to the first component 1. This enables the distance adjustment apparatus to adjust the length of the connection component 200 to shorten or extend. In this solution, the distance adjustment apparatus may be controlled by using an electrical signal to adjust the length of the connection component 200, so that a mobile terminal can be located in a proper position. This improves working effect of the mobile terminal, and improves comfort of using the mobile terminal by a user. In addition, in this application, the length of the connection component 200 can be adjusted in a small course, and a stepless adjustment degree can be almost reached. Therefore, in the conventional technology, a problem that it is difficult for the connection component 200 to reach a comfortable length caused by a large fixed step adjustment manner can be overcome. For example, a watchband has a plurality of successively disposed through holes, and there is a fixed interval between the through holes. Each time a length of the watchband is adjusted, at least a length of the fixed interval is adjusted. Therefore, the problem does not exist in this application.

Figure 7:
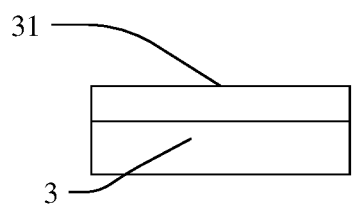
FIG. 7 is a schematic diagram of a structure of a memory alloy component according to an embodiment of this application.

FIG. 7 is a schematic diagram of a structure of a memory alloy component according to an embodiment of this application. As shown in FIG. 7, an elastic material layer 31 is fixedly stacked on the memory alloy component 3. Specifically, the elastic material layer 31 is one-to-one stacked on and fastened to the first memory alloy component 41 of the first driving part 4, and the elastic material layer 31 is also one-to-one stacked on and fastened to the second memory alloy component 51 of the second driving part 5. In this solution, both the first memory alloy component 41 and the second memory alloy component 51 have the elastic material layer 31. The elastic material layer 31 is a high-toughness material, has given elasticity, and may be specifically configured to provide a resetting force after the first memory alloy component 41 and the second memory alloy component 51 deform. When driving forces on the deformation of the first memory alloy component 41 and the second memory alloy component 51 are weakened or disappear, that is, when the temperature is lower than the set threshold, the elastic material layer 31 drives the first memory alloy component 41 and the second memory alloy component 51 to quickly restore to original statues, so that the first memory alloy component 41 and the second memory alloy component 51 deform when the first memory alloy component 41 and the second memory alloy component 51 are driven next time.

Materials of the first memory alloy component 41 and the second memory alloy component 51 may be specifically nickel-titanium memory alloys. The first memory alloy component 41 and the second memory alloy component 51 may deform at a set temperature through a temperature-shape matching design. The elastic material layer 31 is an elastic material layer 31 prepared by the high-toughness material, and the high-toughness material may specifically be an organic matter such as a photosensitive epoxy resin (SU-8), or a high-strength material such as copper, steel, or iron. In other words, the elastic material layer 31 may be a photosensitive epoxy resin elastic material layer, a copper elastic material layer, a steel or iron elastic material layer.

Figure 8:
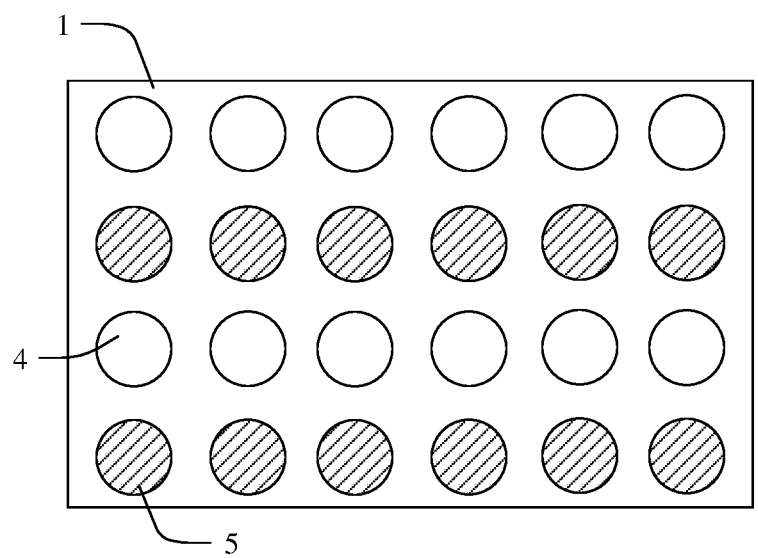
FIG. 8 is a schematic diagram of a partial structure of a distance adjustment apparatus according to an embodiment of this application.

FIG. 8 is a partial schematic diagram of a distance adjustment apparatus according to an embodiment of this application. As shown in FIG. 8, the distance adjustment apparatus may include a plurality of first driving parts 4 and a plurality of second driving parts 5, and the plurality of first driving parts 4 simultaneously drive the second component 2 to move closer to the first component 1. Therefore, a structure of the first driving part 4 can be designed to be small, and a sufficient driving force can still be provided. Further, the second driving part 5 adjusts a small step of moving the second component 2 closer to the first component 1 each time, to tend to be stepless adjustment. The second driving part 5 may also be designed to be small. Details are not described herein. In essence, the first driving part 4 and the second driving part 5 may have a same size or but different structures, and driving in different directions is implemented by using different fastening manners.

First memory alloy components 41 of the plurality of first driving parts 4 may share a set of electrodes. To be specific, a power supply apparatus may simultaneously supply power to the plurality of first memory alloy components 41, and several first memory alloy components 41 may deform at the same time. In this solution, a control process of the distance adjustment apparatus can be simplified, and the driving force on the first driving part 4 can be increased. Similarly, second memory alloy components 51 of the plurality of second driving parts 5 may share a set of electrodes. To be specific, a power supply apparatus may simultaneously supply power to the plurality of second memory alloy components 51, and several second memory alloy components 51 may deform at the same time. In this solution, a control process of the distance adjustment apparatus can be simplified, and the driving force on the second driving part 5 can be increased. A specific setting position of the electrode is not limited, and may be set based on an actual structure.

Figure 9:
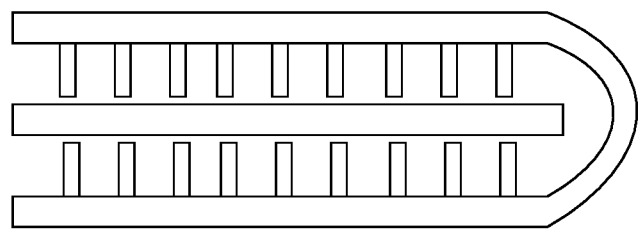
FIG. 9 is a schematic diagram of a cross-sectional structure of a distance adjustment apparatus according to an embodiment of this application.
Figure 10:
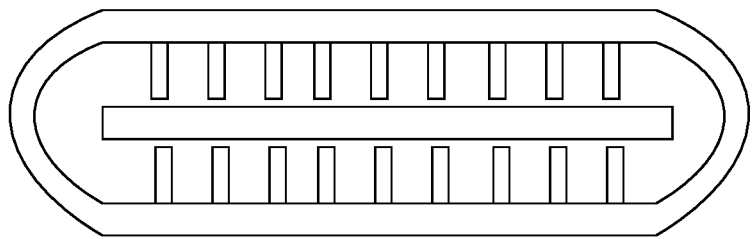
FIG. 10 is a schematic diagram of another cross-sectional structure of a distance adjustment apparatus according to an embodiment of this application.

FIG. 9 is a schematic diagram of a cross-sectional structure of a distance adjustment apparatus according to an embodiment of this application, and FIG. 10 is a schematic diagram of another cross-sectional structure of a distance adjustment apparatus according to an embodiment of this application. Cross sections of FIG. 9 and FIG. 10 are perpendicular to a first direction. Refer to FIG. 9 and FIG. 10. The second component 2 is located between the first driving part 4 and the second driving part 5, that is, the first driving part 4 and the second driving part 5 are located on two sides of the second component 2. In this way, the first driving part 4 on one side of the second component 2 drives the second component 2 to move in the first direction relative to the first component 1, and the second driving part 5 on the other side of the second component 2 drives the second component 2 to move in the second direction relative to the first component 1. This solution helps reduce an area occupied by the distance adjustment apparatus, and the first driving part 4 and the second driving part 5 that are disposed opposite to each other may further cooperate with each other. In this solution, as shown in FIG. 7, the first component 1 may be U-shaped. Alternatively, as shown in FIG. 8, the first component 1 may be tubular, and the second component 2 passes through the middle of the first component 1. Certainly, the first component 1 may alternatively be any structure in which the first driving part 4 and the second driving part 5 may be disposed on the two sides of the second component 2. This is not limited in this application.

Figure 11:
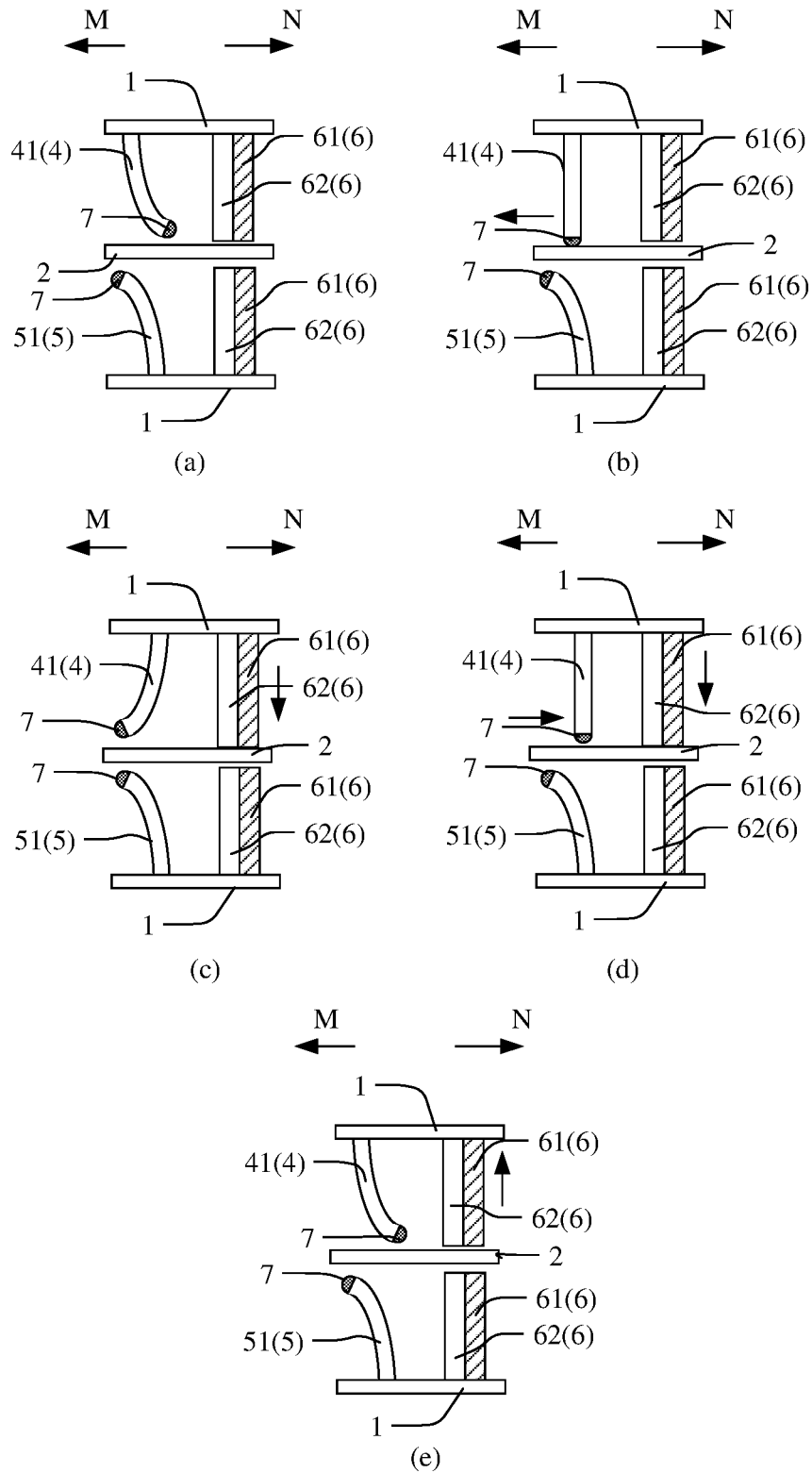
FIG. 11 is a schematic diagram of an operation process of a first driving part according to an embodiment of this application.

FIG. 11 is a schematic diagram of an operation process of a first driving part according to an embodiment of this application. Refer to FIG. 11. The distance adjustment apparatus further includes an auxiliary part 6. The auxiliary part 6 is disposed between the second component 2 and the first component 1. When the auxiliary part 6 is in the first status, the first driving part 4 or the second driving part 5 can be in contact with the second component 2, thereby driving the second component 2 to move closer to the first component 1. When the auxiliary part 6 is in the second status, if there is a gap between the second component 2, and the first driving part 4 or the second driving part 5, the auxiliary part 6 cannot be in contact with the second component 2, and therefore cannot generate a driving force on the second component 2. When the first memory alloy component 41 is bent in the first form in the second direction, and is bent in the second form in the first direction, the first memory alloy component 41 cannot be in contact with the second component 2 in the first form or the second form. However, when the first memory alloy component 41 changes from the first form to the second form, the first memory alloy component 41 needs to be straightened during transition, and in this case, the auxiliary part 6 is in the first status, and the first memory alloy component 41 is in contact with the second component 2. Specifically, when the temperature of the first memory alloy component 41 is lower than the set threshold, the first memory alloy component 41 is in the first form, that is, the first memory alloy component 41 is bent in the second direction, as shown in FIG. 11(a). When the first memory alloy component 41 is powered on, the first memory alloy component 41 changes from the first form to the second form as the temperature rises above the set threshold, that is, the first memory alloy component 41 deforms from bending in the second direction to bending in the first direction. The auxiliary part 6 is in the first form, and the first memory alloy component 41 can abut against the second component 2 during deformation, and generate a friction force on the second component 2 in the first direction, to drive the second component 2 to move in the first direction as shown in FIG. 11(b). Then, the first memory alloy component 41 is bent in the first direction, as shown in FIG. 11(c). When a current of the first memory alloy component 41 is reduced or the power is cut off, the temperature of the first memory alloy component 41 decreases, and when the temperature of the first memory alloy component 41 is lower than the set threshold, the first memory alloy component 41 changes from the second form to the first form, that is, from bending in the first direction to bending in the second direction. In this case, the auxiliary part 6 is in the second status, and there is a specific gap between the first memory alloy component 41 and the second component 2 during deformation, as shown in FIG. 11(d). Therefore, no driving force in the second direction is generated, to ensure that the first driving part 4 can only drive the second component 2 to move in the first direction relative to the first component 1. Then, the first memory alloy component 41 is restored to the first form, as shown in FIG. 11(e). In this way, the first memory alloy component 41 completes deformation for one time, and the second component 2 is moved by a small distance in the first direction relative to the first component 1. Based on a requirement, the current of the first memory alloy component 41 is controlled, for example, a square wave current is input. The first memory alloy component 41 may deform for a plurality of times, to drive the second component 2 to move to a proper position closer to the first component 1.

Figure 12:
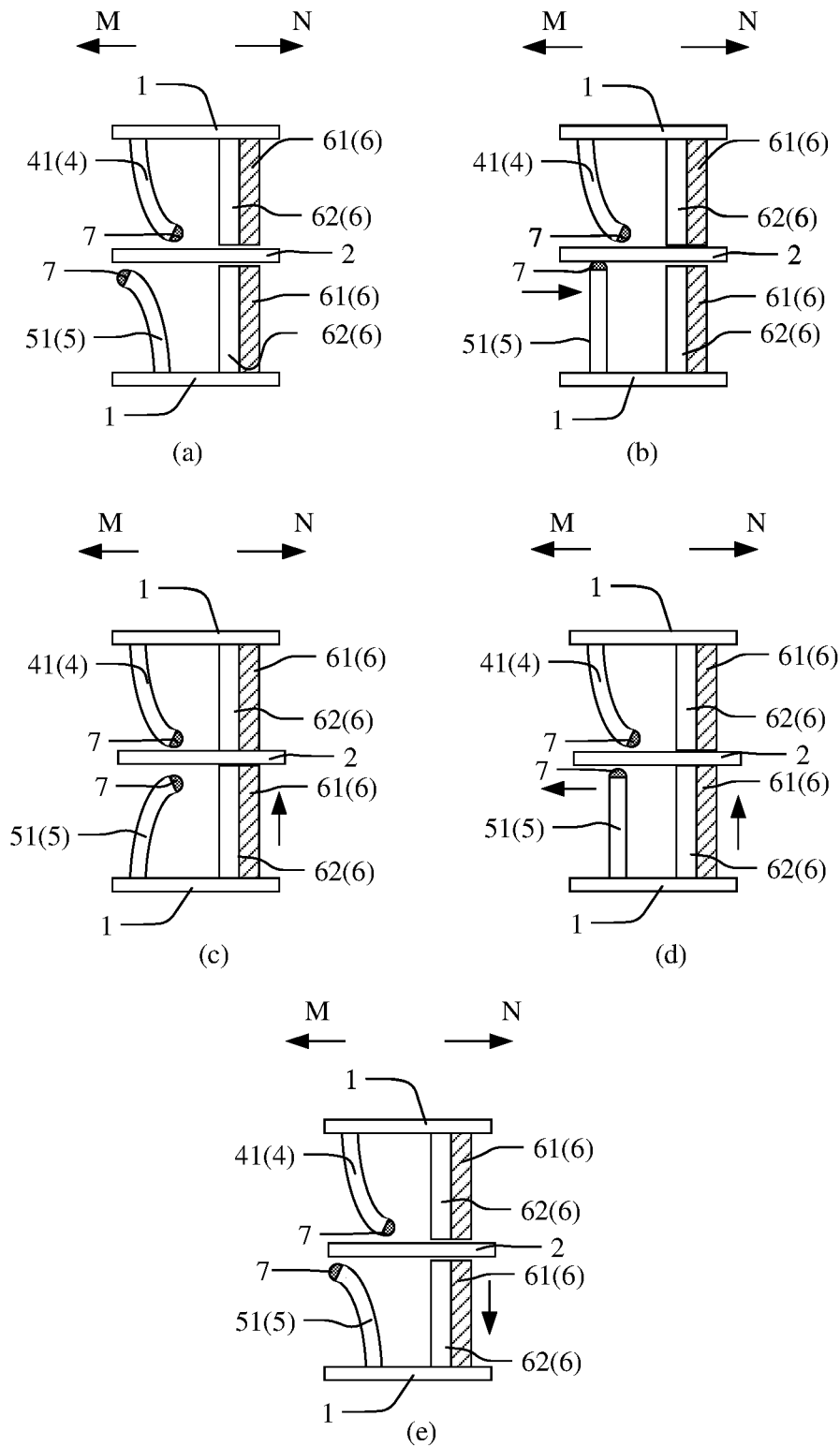
FIG. 12 is a schematic diagram of an operation process of a second driving part according to an embodiment of this application.

FIG. 12 is a schematic diagram of an operation process of a second driving part according to an embodiment of this application. As shown in FIG. 12(a) to FIG. 12(e), a deformation process of the second memory alloy component 51 of the second driving part 5 is opposite to a deformation process of the first memory alloy component 41. When the second memory alloy component 51 is bent in the first form in the second direction, and is bent in the second form in the first direction, the second memory alloy component 51 cannot be in contact with the second component 2 in the second form or the first form. However, when the second memory alloy component 51 changes from the second form to the first form, the second memory alloy component 51 needs to be straightened during transition, and in this case, the auxiliary part 6 is in the first status, and the second memory alloy component 51 is in contact with the second component 2. Specifically, when the temperature of the second memory alloy component 51 is lower than the set threshold, the second memory alloy component 51 is in the second form, that is, the second memory alloy component 51 is bent in the first direction, as shown in FIG. 12(a). When the second memory alloy component 51 is powered on, the second memory alloy component 51 changes from the second form to the first form as the temperature rises above the set threshold, that is, the second memory alloy component 51 deforms from bending in the first direction to bending in the second direction. The auxiliary part 6 is in the first form, and the second memory alloy component 51 can abut against the second component 2 during deformation, and generate a friction force on the second component 2 in the second direction, to drive the second component 2 to move in the second direction as shown in FIG. 12(b). Then, the second memory alloy component 51 is bent in the second direction, as shown in FIG. 12(c). When a current of the second memory alloy component 51 is reduced or the power is cut off, the temperature of the second memory alloy component 51 decreases, and when the temperature of the second memory alloy component 51 is lower than the set threshold, the second memory alloy component 51 changes from the first form to the second form, that is, from bending in the second direction to bending in the first direction. In this case, the auxiliary part 6 is in the second status, and there is a specific gap between the second memory alloy component 51 and the second component 2 during deformation, as shown in FIG. 12(d). Therefore, no driving force in the first direction is generated, to ensure that the second driving part 5 can only drive the second component 2 to move in the second direction relative to the first component 1. Then, the second memory alloy component 51 is restored to the second form, as shown in FIG. 12(e). In this way, the second memory alloy component 51 completes deformation for one time, and the second component 2 is moved by a small distance in the second direction relative to the first component 1. Based on a requirement, the current of the second memory alloy component 51 is controlled, for example, a square wave current is input. The second memory alloy component 51 may deform for a plurality of times, to drive the second component 2 to move to a proper position closer to the first component 1. This embodiment shows an embodiment in which the first driving part 4 and the second driving part 5 are disposed on the two sides of the second component 2.

In this technical solution, the distance adjustment apparatus may generate the driving force in the first direction and the driving force in the second direction on the second component 2, and may perform active adjustment in both directions. In other words, the connection component 200 may be adjusted to extend or shorten, to be applied to rich use scenarios. The connection component 200 has a good use feeling.

Figure 13:
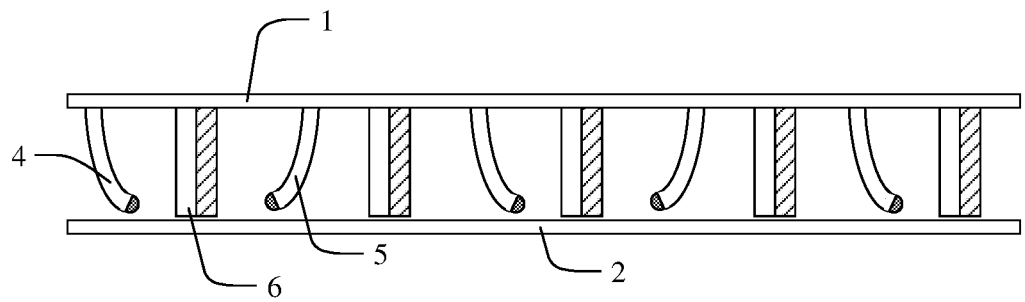
FIG. 13 is a schematic diagram of another structure of a distance adjustment apparatus according to an embodiment of this application.

FIG. 13 is another schematic diagram of a structure of a distance adjustment apparatus according to an embodiment of this application. Refer to FIG. 13, the first driving part 4 and the second driving part 5 may be disposed on a same side of the second component 2. In this case, the auxiliary part 6 is disposed. The auxiliary part 6 may have one end fastened to the first component 1 and the other end facing the second component 2. When the auxiliary part 6 is in the first status, a length of the auxiliary part 6 in a direction from the first component 1 to the second component 2 is a first length, and the first driving part 4 and the second driving part 5 can be in contact with the second component 2. When the auxiliary part 6 is in the second status, the length of the auxiliary part 6 in the direction from the first component 1 to the second component 2 is a second length, and the second length is greater than the first length. In this case, the auxiliary part 6 can drive the second component 2 to move in a direction away from a surface of the first component 1, so that there is a gap between the second component 2, and the first driving part 4 and the second driving part 5. No matter how the first memory alloy component 41 and the second memory alloy component 51 deform, no force is generated on the second component 2, so that the first memory alloy component 41 and the second memory alloy component 51 can generate a force in one direction on the second component 2.

In another embodiment, refer to FIG. 12. The second component 2 is located between the first driving part 4 and the second driving part 5, one end of the auxiliary part 6 is fastened to the first component 1, and the other end faces the second component 2. Specifically, the auxiliary part 6 includes a first auxiliary part and a second auxiliary part. The first auxiliary part and the first driving part 4 are located on a same side and operate in cooperation with the first driving part 4, and the second auxiliary part and the second driving part 5 are located on a same side and operate in cooperation with the second driving part 5. Specifically, when the first auxiliary part is in the first status, a length of the first auxiliary part in a direction from the first component 1 to the second component 2 is a first length, and the first driving part 4 can be in contact with the second component 2. When the first auxiliary part is in the second status, the length of the first auxiliary part in the direction from the first component 1 to the second component 2 is a second length, and the second length is greater than the first length. In this case, the first auxiliary part can drive the second component 2 to move in a direction away from the first driving part 4, and there is a gap between the first driving part 4 and the second component 2, so that when the first memory alloy component 41 changes from the second form to the first form, the first memory alloy component 41 does not generate a driving force on the second component 2. Similarly, when the second auxiliary part is in the first status, a length of the first auxiliary part in a direction from the first component 1 to the second component 2 is a first length, and the second driving part 5 can be in contact with the second component 2. When the first auxiliary part is in the second status, the length of the second auxiliary part in the direction from the first component 1 to the second component 2 is a second length, and the second length is greater than the first length. In this case, the second auxiliary part can drive the second component 2 to move in a direction away from the second driving part 5, and there is a gap between the first driving part 4 and the second component 2, so that when the second memory alloy component 51 changes from the first form to the second form, the second memory alloy component 51 does not generate a driving force on the second component 2.

Refer to FIG. 11 and FIG. 12. When the auxiliary part 6 is specifically disposed, the auxiliary part 6 includes a first memory alloy spring 61, the first memory alloy spring 61 is connected to two electrodes, and the first memory alloy spring 61 may be connected to a circuit by using the two electrodes. In this way, a temperature of the first memory alloy spring 61 is controlled by a current. Specifically, when the temperature of the first memory alloy spring 61 is lower than a set threshold, the first memory alloy spring 61 is not powered on or is powered on by using a small amount of power, the first memory alloy spring 61 is of the first length, and the auxiliary part 6 is in the first status. When the temperature of the first memory alloy spring 61 is higher than the set threshold, the first memory alloy spring 61 is powered on or is powered on by using a large amount of power, the first memory alloy spring 61 extends towards the second component 2 to the second length, the second length is greater than the first length, the auxiliary part 6 is in the second status, and the first memory alloy spring 61 can drive the second component 2 to move in the direction away from the surface of the first component 1. In this solution, the deformation of the first memory alloy spring 61 can be controlled by controlling the current of the first memory alloy spring 61, and specifically, the current of the first memory alloy spring 61 is opposite to the square wave current of the first driving part 4 or the second driving part 5 in cooperation with the first memory alloy spring 61. In other words, when the current of the first driving part 4 or the second driving part 5 is large, the current of the corresponding first memory alloy spring 61 is small or there is no current. When the current of the first driving part 4 or the second driving part 5 is small or there is no current, the current of the corresponding first memory alloy spring 61 is large.

Still refer to FIG. 11 and FIG. 12. The auxiliary part 6 further includes a first return spring 62, and the first return spring 62 may be a common spring. The first return spring 62 is disposed in parallel with the first memory alloy spring 61. When the first memory alloy spring 61 is of the first length, the first return spring 62 is in an energy release state, and the first return spring 62 has no force on the first memory alloy spring 61. When the first memory alloy spring 61 is of the second length, the first return spring 62 is in an energy storage state, and when the current of the first memory alloy spring 61 is reduced or the power is off, the first memory alloy spring 61 may be quickly restored to the first status under an action of the first return spring 62, that is, the first length. This solution is advantageous in reducing influence of the first memory alloy spring 61 on a position of the second component 2. It is convenient to make a next operation cycle of the first driving part 4 and the second driving part 5 proceed as soon as possible, thereby improving adjustment efficiency of the distance adjustment apparatus.

Further, still refer to FIG. 11 and FIG. 12. Drive efficiency is improved to improve the friction force when the first driving part 4 and the second driving part 5 drive the second component 2. An elastic layer 7 may be disposed at one end of the first driving part 4 towards the second component 2, and the elastic layer 7 may be disposed at one end of the second driving part 5 towards the second component 2. The elastic layer 7 may be specifically copper or iron. Compared with a material of the memory alloy component 3, the elastic layer 7 is more elastic, and may generate a large friction force with the second component 2, so that the first driving part 4 and the second driving part 5 drive the second component 2 to move closer to the first component 1.

Figure 14:
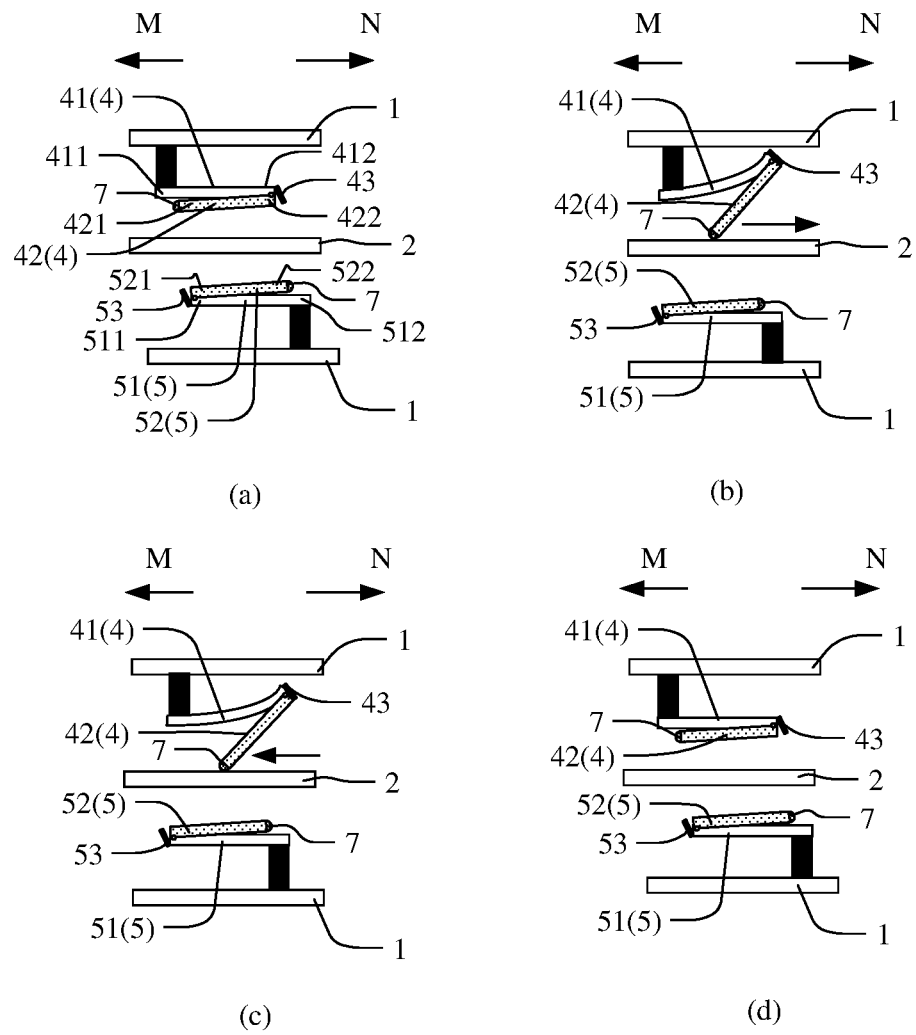
FIG. 14 is a schematic diagram of an operation process of a first driving part according to an embodiment of this application.

FIG. 14 is a schematic diagram of an operation process of a first driving part according to an embodiment of this application. Refer to FIG. 14. When the first memory alloy component 41 is not powered on or is powered on by using a small amount of power, the first memory alloy component 41 is in the first form. Specifically, the first memory alloy component 41 is parallel to the first direction, as shown in FIG. 14(a). When the first memory alloy component 41 is powered on by using a large amount of power, the first memory alloy component 41 is in the second form. Specifically, the second memory alloy component 51 is bent in a direction away from the second component 2, as shown in FIG. 14(b). Specifically, the first memory alloy component 41 includes a first end 411 and a second end 412 that are distributed in the second direction. In other words, the second end 412 is located in the second direction of the first end 411, and the first end 411 is fastened to the first component 1. The first driving part 4 further includes a first linkage rod 42. The first linkage rod 42 includes a third end 421 and a fourth end 422 that are distributed in the second direction, that is, the fourth end 422 is located in the second direction of the third end 421. The second end 412 is rotatably connected to the fourth end 422, so that the first linkage rod 42 can rotate closer to the first memory alloy component 41, and a first baffle 43 is fastened to the second end 412. When the first memory alloy component 41 changes from the second form to the first form, the fourth end 422 abuts against the first baffle 43, the third end 421 abuts against the second component 2, and the third end 421 drives the second component 2 to move in the first direction. Specifically, when the first memory alloy component 41 is not powered on, the first memory alloy component 41 is in the first form, that is, the first memory alloy component 41 is parallel to the first direction, as shown in FIG. 14(a). When the first memory alloy component 41 is powered on by using the large amount of power, the first memory alloy component 41 changes from the first form to the second form, that is, the first memory alloy component 41 is bent in the direction away from the second component 2, as shown in FIG. 14(b). In the process, because the first linkage rod 42 is rotatably connected to the first memory alloy component 41, a friction force between the first linkage rod 42 and the second component 2 is small, and the second component 2 is not enabled to move in the second direction. Then, the amount of power supplied to the first memory alloy component 41 is reduced or the power is off, and the first memory alloy component 41 changes from the second form to the first form, that is, the first memory alloy component 41 changes from a bent state to a straight state. The fourth end 422 of the first linkage rod 42 abuts against the first baffle 43, and the third end 421 abuts against the second component 2 to generate a large friction force, so that the first driving part 4 can drive the second component 2 to move in the first direction relative to the first component 1, as shown in FIG. 14(c). Then, the first memory alloy component 41 is restored to the first form, as shown in FIG. 14(d). In this way, the first memory alloy component 41 completes deformation for one time, and the second component 2 is moved by a small distance in the first direction relative to the first component 1. Based on a requirement, the current of the first memory alloy component 41 is controlled, for example, a square wave current is input. The first memory alloy component 41 may deform for a plurality of times, to drive the second component 2 to move to a proper position closer to the first component 1.

Figure 15:
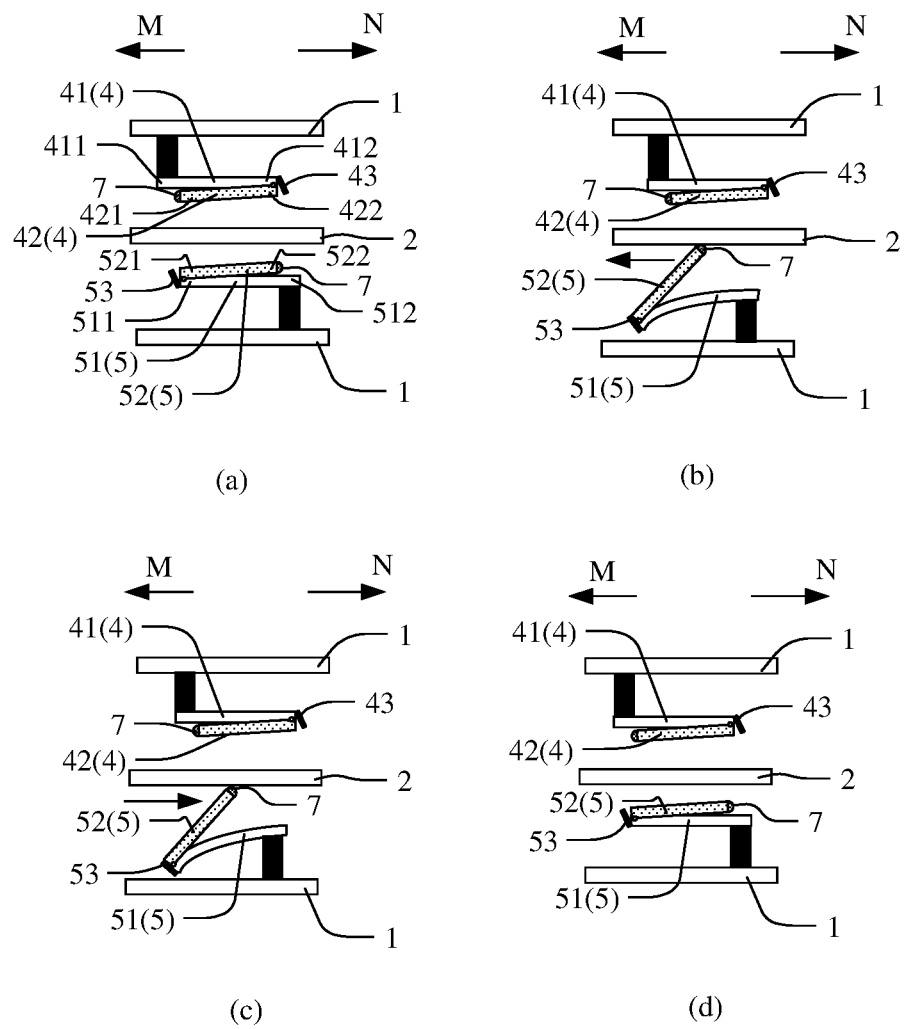
FIG. 15 is a schematic diagram of an operation process of a second driving part according to an embodiment of this application.

FIG. 15 is a schematic diagram of an operation process of a second driving part according to an embodiment of this application. Refer to FIG. 15. When the second memory alloy component 51 is not powered on or is powered on by using a small amount of power, the temperature of the second memory alloy component 51 is lower than the set threshold, and the second memory alloy component 51 is in the first form. Specifically, the second memory alloy component 51 is parallel to the first direction, as shown in FIG. 15(a). When the second memory alloy component 51 is powered on by using a large amount of power, the temperature of the second memory alloy component 51 is higher than the set threshold, and the second memory alloy component 51 is in the second form. Specifically, the second memory alloy component 51 is bent in a direction away from the second component 2, as shown in FIG. 15(b). Specifically, the second memory alloy component 51 includes a fifth end 511 and a sixth end 512 that are distributed in the second direction. In other words, the sixth end 512 is located in the second direction of the fifth end 511, and the sixth end 512 is fastened to the first component 1. The second driving part 5 further includes a second linkage rod 52. The second linkage rod 52 includes a seventh end 521 and an eighth end 522 that are distributed in the second direction, that is, the eighth end 522 is located in the second direction of the seventh end 521. The fifth end 511 is rotatably connected to the seventh end 521, so that the second linkage rod 52 can rotate closer to the second memory alloy component 51, and the second baffle 53 is fastened to the fifth end 511. When the second memory alloy component 51 changes from the second form to the first form, the seventh end 521 abuts against the second baffle 53, the eighth end 522 abuts against the second component 2, and the eighth end 522 drives the second component 2 to move in the second direction. Specifically, when the second memory alloy component 51 is not powered on, the second memory alloy component 51 is in the first form, that is, the second memory alloy component 51 is parallel to the first direction, as shown in FIG. 15(a). When the second memory alloy component 51 is powered on by using the large amount of power, the second memory alloy component 51 changes from the first form to the second form, that is, the second memory alloy component 51 is bent in the direction away from the second component 2, as shown in FIG. 15(b). In the process, because the second linkage rod 52 is rotatably connected to the second memory alloy component 51, a friction force between the second linkage rod 52 and the second component 2 is small, and the second component 2 is not enabled to move in the second direction. Then, the amount of power supplied to the second memory alloy component 51 is reduced or the power is off, and the second memory alloy component 51 changes from the second form to the first form, that is, the second memory alloy component 51 changes from a bent state to a straight state. The seventh end 521 of the second linkage rod 52 abuts against the second baffle 53, and the eighth end 522 abuts against the second component 2 to generate a large friction force, so that the second driving part 5 can drive the second component 2 to move in the second direction relative to the first component 1, as shown in FIG. 15(c). The second memory alloy component 51 is restored to the first form, as shown in FIG. 15(d). In this way, the second memory alloy component 51 completes deformation for one time, and the second component 2 is moved by a small distance in the second direction relative to the first component 1. Based on a requirement, the current of the second memory alloy component 51 is controlled, for example, a square wave current is input. The second memory alloy component 51 may deform for a plurality of times, to drive the second component 2 to move to a proper position closer to the first component 1.

Further, still refer to FIG. 14 and FIG. 15. Drive efficiency is improved to improve the friction force when the first driving part 4 and the second driving part 5 drive the second component 2. The elastic layer 7 may be disposed at one end of the first driving part 4 facing the second component 2, that is, the third end 421 of the first linkage rod 42 has the elastic layer 7. The elastic layer 7 may also be disposed at one end of the second driving part 5 facing the second component 2, that is, the eighth end of the second linkage rod 52 has the elastic layer 7. The elastic layer 7 may be specifically copper or iron. Compared with a material of the memory alloy component, the elastic layer 7 is more elastic, and may generate a large friction force with the second component 2, so that the first driving part 4 and the second driving part 5 drive the second component 2 to move closer to the first component 1.

Figure 16:
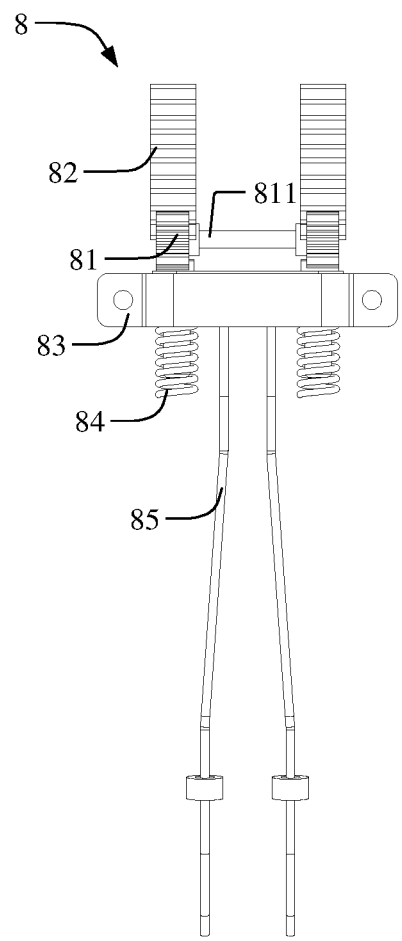
FIG. 16 is a schematic diagram of a structure of a stop structure according to an embodiment of this application.

FIG. 16 is a schematic diagram of a structure of a stop structure according to an embodiment of this application. Refer to FIG. 16. The distance adjustment apparatus further includes the stop structure 8. The stop structure 8 is disposed between the first component 1 and the second component 2. When the stop structure 8 is in the first status, the second component 2 can move closer to the first component 1. To be specific, the distance adjustment apparatus can adjust a distance between the first component 1 and the second component 2. When the stop structure 8 is in the second status, the stop structure 8 is fixedly connected to the second component 2 and the first component 1, that is, the second component 2 and the first component 1 cannot move closer to each other. The distance adjustment apparatus cannot adjust the distance between the first component 1 and the second component 2. Therefore, when the length of the connection component 200 of the distance adjustment apparatus needs to be adjusted, the stop structure 8 is in the first status, and the length of the connection component 200 is adjusted by the distance adjustment apparatus. When the distance adjustment apparatus adjusts the length of the connection component 200 to meet a use requirement, the stop structure 8 is in the second status, so that the connection component 200 is maintained at a required length.

Figure 17:
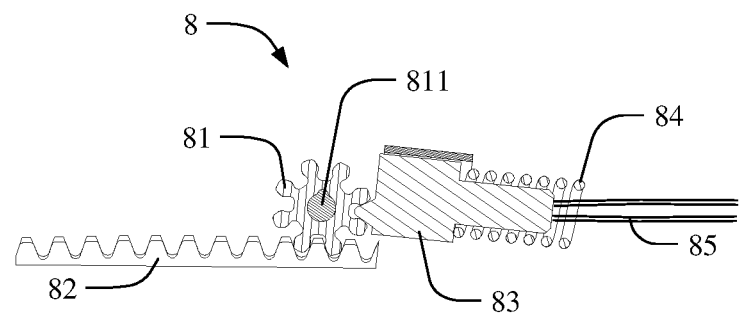
FIG. 17 is a schematic diagram of a cross-sectional structure of a stop structure according to an embodiment of this application.

FIG. 17 is a schematic diagram of a cross-sectional structure of a stop structure according to an embodiment of this application. With reference to FIG. 16 and FIG. 17, when the stop structure 8 is specifically disposed, a memory alloy structure 85 may also be used in the stop structure 8 to implement an action of electrically driving the stop structure 8, so that the stop structure 8 can be controlled by a controller to implement a stop function after adjustment of a position adjustment apparatus is complete. As shown in FIG. 16, the stop structure 8 includes a gear 81, a rack 82, a clamping member 83, an elastic member 84, and a memory alloy structure 85, where the gear 81 and the rack 82 are adapted, and the gear 81 can mesh with and roll on the rack 82. The rack 82 is fastened to the first component 1, and a rotating shaft 811 of the gear 81 is fastened to the second component 2. Specifically, the gear 81 is rotatably connected to the rotating shaft 811. To be specific, when the gear 81 rotates, the rotating shaft 811 does not rotate, but in a rotation process of the gear 81, the rotating shaft 811 moves relative to the rack 82 at the same time. In this case, the rotating shaft 811 may move with the gear 81, so that the second component 2 and the first component 1 may be driven to move closer to each other. If the gear 81 cannot rotate, the rotating shaft 811 cannot move with the gear 81. The first component 1 and the second component 2 are relatively fastened to implement the stop function.

The clamping member 83 of the stop structure 8 can be engaged with the gear 81, the memory alloy structure 85 is connected between the clamping member 83 and the second component 2, and the elastic member 84 is also disposed between the clamping member 83 and the second component 2. When no current is applied to the memory alloy structure 85 or the current applied to the memory alloy structure 85 is small, a temperature of the memory alloy structure 85 may be lower than a set threshold, the memory alloy structure 85 is in the first form, and the clamping member 83 is engaged with the gear 81. In this case, the elastic member 84 drives the clamping member 83 to engage with the gear 81, and therefore a driving force on the first driving part 4 or a driving force on the second driving part 5 cannot overcome a clamping function of the clamping member 83. In this way, the first component 1 and the second component 2 may be more reliably in a stopped state. When a given current is applied to the memory alloy structure 85, the temperature of the memory alloy structure 85 may be higher than the preset threshold. The memory alloy structure 85 is in the second form, and can drive the clamping member 83 to move away from the gear 81. In this case, the clamping member 83 is separated from the gear 81, the gear 81 can mesh with the rack 82, the distance adjustment apparatus may drive the second component 2 to move closer to the first component 1, and the elastic member 84 is in the energy storage state. When the current of the memory alloy structure 85 is reduced or cut off, the temperature of the memory alloy structure 85 is reduced, and when the temperature of the memory alloy structure 85 is lower than the set threshold, under an action of the elastic member 84 in the energy storage state, the clamping member 83 moves closer to the gear 81 and engages with the gear 81, thereby implementing the stop function of the stop structure 8.

In another embodiment, the rack 82 may be fixedly disposed on the second component 2, and the rotating shaft 811 of the gear 81 may be fixedly disposed on the first component 1. The elastic member 84 is disposed between the clamping member 83 and the first component 1, and the memory alloy structure 85 is connected between the clamping member 83 and the first component 1. In conclusion, the elastic member 84, the memory alloy structure 85, and the gear 81 are disposed in a same component, and are all disposed in the first component 1 or in the second component 2. A startup process is similar. Details are not described herein again.

Still refer to FIG. 16. In a specific embodiment, two groups of gears 81 and racks 82 that move synchronously may be included, that is, two gears 81 and two racks 82 are included. The clamping member 83 may be engaged with the two gears 81 at the same time. Therefore, the stop structure 8 can have better stability.

In a specific embodiment, a specific structure of the memory alloy structure 85 is not limited, provided that the clamping member 83 can be driven to move. In the embodiment shown in FIG. 16, the memory alloy structure 85 is a memory alloy wire. By controlling deformation of the memory alloy wire, the clamping member 83 may be pulled, so that the clamping member 83 is separated from the gear 81.

The foregoing embodiment is merely a specific embodiment. In another embodiment, the stop structure 8 may alternatively be of another specific structure, for example, any form such as a bayonet buckle assembly or a cylinder assembly, provided that the stop function can be implemented.

Figure 18:
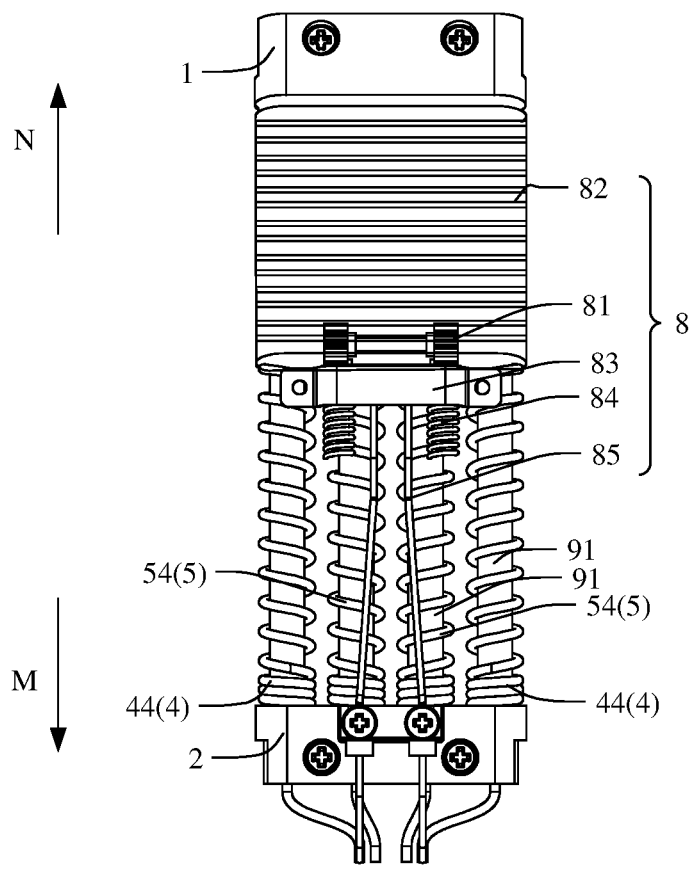
FIG. 18 is a schematic diagram of another structure of a distance adjustment apparatus according to an embodiment of this application.
Figure 19:
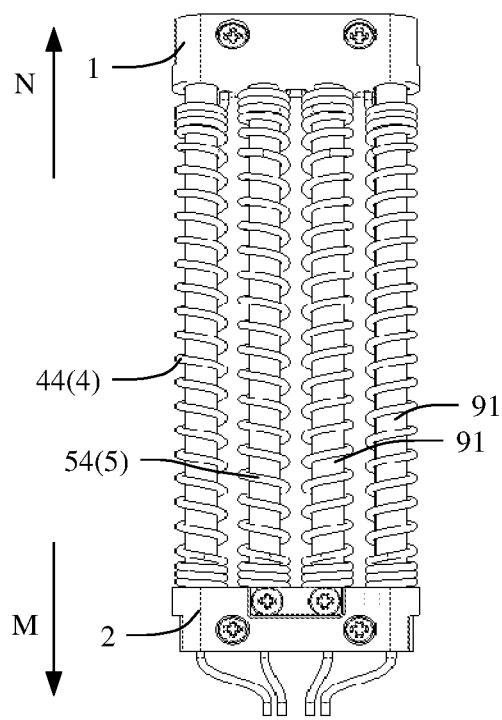
FIG. 19 is a schematic diagram of a partial structure of a specific adjustment apparatus according to an embodiment of this application.

FIG. 18 is a schematic diagram of another structure of a distance adjustment apparatus according to an embodiment of this application, and FIG. 19 is a schematic diagram of a partial structure of a specific adjustment apparatus according to an embodiment of this application. As shown in FIG. 18 and FIG. 19, this application further provides another distance adjustment apparatus. FIG. 19 shows the structure of the apparatus when no stop structure is provided. The distance adjustment apparatus includes the first component 1, the second component 2, a second memory alloy spring 44, a second return spring 54, and the stop structure 8, where the second component 2 is movably mounted on the first component 1, that is, the second component 2 can move closer to the first component 1. The second component 2 and the first component 1 move closer to each other or away from each other. The second memory alloy spring 44 is equivalent to the first driving part 4, and the second return spring 54 is equivalent to the second driving part 5.

The second memory alloy spring 44 can drive the second component 2 to move in the first direction relative to the first component 1, and the second return spring 54 can drive the second component 2 to move in the second direction relative to the first component 1, where the first direction is opposite to the second direction. Specifically, one end of the second memory alloy spring 44 is connected to the first component 1, and the other end is connected to the second component 2. The second memory alloy spring 44 is connected to two electrodes, and the second memory alloy spring 44 may be connected to a circuit by using the two electrodes. A given current may be applied to the second memory alloy spring 44, so that a temperature of the second memory alloy spring 44 may rise, and deformation occurs, to drive the first component 1 to move in the first direction relative to the first component 1. One end of the second return spring 54 is connected to the first component 1, and the other end is connected to the second component 2. After the temperature of the second memory alloy spring 44 rises, the second component 2 is driven to move in the first direction relative to the first component 1. The second return spring 54 can drive the second component 2 to move in the second direction relative to the first component 1, where the first direction is opposite to the second direction. The stop structure 8 is disposed between the first component 1 and the second component 2. When the stop structure 8 is in the first status, the second component 2 can move closer to the first component 1. To be specific, the distance adjustment apparatus can adjust a distance between the first component 1 and the second component 2. When the stop structure 8 is in the second status, the stop structure 8 is fixedly connected to the second component 2 and the first component 1, that is, the second component 2 and the first component 1 cannot move closer to each other. The distance adjustment apparatus cannot adjust the distance between the first component 1 and the second component 2. Therefore, when the length of the connection component 200 of the distance adjustment apparatus needs to be adjusted, the stop structure 8 is in the first status, and the length of the connection component 200 is adjusted by the distance adjustment apparatus. When the distance adjustment apparatus adjusts the length of the connection component 200 to meet a use requirement, the stop structure 8 is in the second status, so that the connection component 200 is maintained at a required length.

The following describes a working process of the foregoing distance adjustment apparatus. In a specific embodiment, when no current is applied to the second memory alloy spring 44 or the current applied to the second memory alloy spring 44 is small, the temperature of the second memory alloy spring 44 is lower than a set threshold, and the second memory alloy spring 44 is of the first length. In this case, the distance adjustment apparatus is considered to be in an initial status, and the stop structure 8 is in the first status. When a given current is applied to the second memory alloy spring 44, the temperature of the second memory alloy spring 44 rises, and when the temperature of the second memory alloy spring 44 is higher than the set threshold, the second memory alloy spring 44 telescopically deforms in the first direction to the second length, where the second length is different from the first length. Therefore, the second memory alloy spring 44 can drive the second component 2 to move in the first direction relative to the first component 1. When the second component 2 moves to a set position in the first direction relative to the first component 1, the stop structure 8 may be switched to the second status, so that the second component 2 and the first component 1 are relatively fastened. In this case, the second memory alloy spring 44 may be powered off. When it is needs to move the second component 2 in the second direction relative to the first component 1, the stop structure 8 is switched to the first status, and the second return spring 54 drives the second component 2 to move in the second direction relative to the first component 1. When the second component 2 moves to the set position in the second direction relative to the first component 1, the stop structure 8 may be switched to the second status, so that the second component 2 and the first component 1 are relatively fastened. Through cooperation of the second memory alloy spring 44, the second return spring 54, and the stop structure 8, the connection component 200 may be set to a proper length.

The second memory alloy spring 44 may be disposed between the first component 1 and the second component 2. To be specific, the second memory alloy spring 44 and the second return spring 54 are used to drive the second component 2 to move closer to or away from the first component 1. Based on a mounting position of the second memory alloy spring 44, the second memory alloy spring 44 can provide a pushing force for the second component 2. In this case, the second length is greater than the first length. Alternatively, the second memory alloy spring 44 may provide a pulling force for the second component 2. In this case, the second length is less than the first length. This is not limited in this application.

In another embodiment, the distance adjustment apparatus may include two groups of second memory alloy springs 44 and second return springs 54, and the two groups of second memory alloy springs 44 and second return springs 54 are symmetrically disposed at two ends of the second component 2. Specifically, the second component 2 includes a first end and a second end, one group of second memory alloy springs 44 and second return springs 54 are connected to the first end, and another group of second memory alloy springs 44 and second return springs 54 are connected to the second end. In this solution, it may be considered that the first component 1 of the specific adjustment apparatus includes two parts: a first part and a second part, and the second component 2 is disposed between the first part and the second part of the first component 1. Specifically, the second component 2 and the first part are connected by using one group of second memory alloy springs 44 and second return springs 54, and the second component 2 and the second part are connected by using another group of second memory alloy springs 44 and second return springs 54. In this solution, two groups of driving structures may be used to drive the second component 2 to move closer to or away from the first component 1. During actual work, the second memory alloy springs 44 at two ends of the second component 2 simultaneously drive the second component 2 to move, for example, one group of second memory alloy springs 44 extend to provide the pushing force, and the other group of second memory alloy springs 44 retract to provide the pulling force. A working process of the second return spring 54 is similar. When the second return spring 54 drives the second component 2 to return, one of the two groups of second return springs 54 at both ends of the second component 2 provides the pushing force, and the other group of second return springs 54 provides the pulling force.

A specific structure of the second return spring 54 is not limited, and may be a common spring. After the second memory alloy spring 44 drives the second component 2 to move, the common spring may store energy to drive the second component 2 to move in the second direction relative to the first component 1. The second return spring 54 may alternatively be a second return spring 54 made of a memory alloy material, and the second return spring 54 made of the memory alloy material may include two electrodes, which are used to supply a current, to deform the second return spring 54 made of the memory alloy material. In this way, the second component 2 is driven to move in the second direction relative to the first component 1. In this solution, the second return spring 54 may also be prepared by using a memory alloy material, so that the second return spring 54 is controlled to work by using an electric signal. In other words, movement of the second component 2 closer to the first component 1 in two directions may be controlled by using the electric signal, and this helps improve controllability of the distance adjustment apparatus.

Refer to FIG. 18. When the distance adjustment apparatus is specifically disposed, the distance adjustment apparatus further includes a first guide member 9, where the first guide member 9 extends in the first direction, and the second return spring 54 and the second memory alloy spring 44 are mounted to the first guide member 9. The first guide member 9 may provide a guiding function for the second return spring 54 and the second memory alloy spring 44, to improve reliability of a direction in which the second return spring 54 and the second memory alloy spring 44 telescopically deform, that is, to ensure that the second memory alloy spring 44 extends and retracts in the first direction and the second direction, and the second return spring 54 extends and retracts in the first direction and the second direction, where distortion is not easily generated. This improves stability of the distance adjustment apparatus.

A total quantity of second memory alloy springs 44 and second return springs 54 is at least three, for example, including two second memory alloy springs 44 and one second return spring 54, including one second memory alloy spring 44 and two second return springs 54, including two second memory alloy springs 44 and two second return springs 54, and including two second memory alloy springs 44 and three second return springs 54. This is not listed one by one in this application. Cooperation of a plurality of second memory alloy springs 44 and second return springs 54 helps improve the reliability of the distance adjustment apparatus, and the second component 2 is not easily deviated.

The second memory alloy springs 44 may share a set of electrodes. To be specific, a power supply apparatus may simultaneously supply power to the plurality of second memory alloy springs 44, and several second memory alloy springs 44 may deform at the same time. In this solution, a control process of the distance adjustment apparatus can be simplified. Similarly, when the second return springs 54 are second return springs 54 made of a memory alloy material, a set of electrodes is shared. A specific setting position of the electrode is not limited, and may be set based on an actual structure. For example, the electrode may be set at one end of the distance adjustment apparatus, to facilitate access to a power supply.

When the distance adjustment apparatus includes at least three second memory alloy springs 44 and second return springs 54, an arrangement manner of the second memory alloy springs 44 and the second return springs 54 is not limited. In an embodiment, the second memory alloy springs 44 and the second return springs 54 are spaced one by one, so that a driving force on the second component 2 closer to the first component 1 in the first direction is uniform, and a driving force on the second component 2 closer to the first component 1 in the second direction is also uniform. In another embodiment, the second memory alloy springs 44 are symmetrically arranged about a symmetry axis of the second component 2, the second return springs 54 are symmetrically arranged about the symmetry axis of the second component 2, and the symmetry axis extends in the first direction. In this solution, the driving force on the second component 2 closer to the first component 1 in the first direction is uniform, and the driving force on the second component 2 closer to the first component 1 in the second direction is also uniform.

With reference to FIG. 16 and FIG. 17, when the stop structure 8 is specifically disposed, the memory alloy structure 85 may also be used in the stop structure 8 to implement the action of electrically driving the stop structure 8, so that the stop structure 8 can be controlled by the controller to implement the stop function after adjustment of the position adjustment apparatus is complete. As shown in FIG. 16, the stop structure 8 includes the gear 81, the rack 82, the clamping member 83, the elastic member 84, and the memory alloy structure 85, where the gear 81 and the rack 82 are adapted, and the gear 81 can mesh with and roll on the rack 82. The rack 82 is fastened to the first component 1, and the rotating shaft 811 of the gear 81 is fastened to the second component 2. Specifically, the gear 81 is rotatably connected to the rotating shaft 811. To be specific, when the gear 81 rotates, the rotating shaft 811 does not rotate, but in the rotation process of the gear 81, the rotating shaft 811 moves relative to the rack 82 at the same time. In this case, the rotating shaft 811 may move with the gear 81, so that the second component 2 and the first component 1 may be driven to move closer to each other. If the gear 81 cannot rotate, the rotating shaft 811 cannot move with the gear 81. The first component 1 and the second component 2 are relatively fastened to implement the stop function.

The clamping member 83 of the stop structure 8 can be engaged with the gear 81, the memory alloy structure 85 is connected between the clamping member 83 and the second component 2, and the elastic member 84 is also disposed between the clamping member 83 and the second component 2. When no current is applied to the memory alloy structure 85 or the current applied to the memory alloy structure 85 is small, the temperature of the memory alloy structure 85 may be lower than the set threshold, the memory alloy structure 85 is in the first form, and the clamping member 83 is engaged with the gear 81. In this case, the elastic member 84 drives the clamping member 83 to engage with the gear 81, and therefore the driving force on the first driving part 4 or the driving force on the second driving part 5 cannot overcome the clamping function of the clamping member 83. In this way, the first component 1 and the second component 2 may be more reliably in the stopped state. When the given current is applied to the memory alloy structure 85, the temperature of the memory alloy structure 85 may be higher than the preset threshold. The memory alloy structure 85 is in the second form, and can drive the clamping member 83 to move away from the gear 81. In this case, the clamping member 83 is separated from the gear 81, the gear 81 can mesh with the rack 82, the distance adjustment apparatus may drive the second component 2 to move closer to the first component 1, and the elastic member 84 is in the energy storage state. When the current of the memory alloy structure 85 is reduced or cut off, the temperature of the memory alloy structure 85 is reduced, and when the temperature of the memory alloy structure 85 is lower than the set threshold, under the action of the elastic member 84 in the energy storage state, the clamping member 83 moves closer to the gear 81 and engages with the gear 81, thereby implementing the stop function of the stop structure 8.

In another embodiment, the rack 82 may be fixedly disposed on the second component 2, and the rotating shaft 811 of the gear 81 may be fixedly disposed on the first component 1. The elastic member 84 is disposed between the clamping member 83 and the first component 1, and the memory alloy structure 85 is connected between the clamping member 83 and the first component 1. In conclusion, the elastic member 84, the memory alloy structure 85, and the gear 81 are disposed in the same component, and are all disposed in the first component 1 or in the second component 2. The startup process is similar. Details are not described herein again.

Refer to FIG. 18. In a specific embodiment, a surface of the rack 82 that adapts to the gear 81 may be prepared on the surface of the second component 2 or the first component 1, thereby simplifying the structure of the distance adjustment apparatus.

The foregoing embodiment is merely a specific embodiment. In another embodiment, the stop structure 8 may alternatively be of another specific structure, for example, any form such as the bayonet buckle assembly or the cylinder assembly, provided that the stop function can be implemented.

Figure 20:
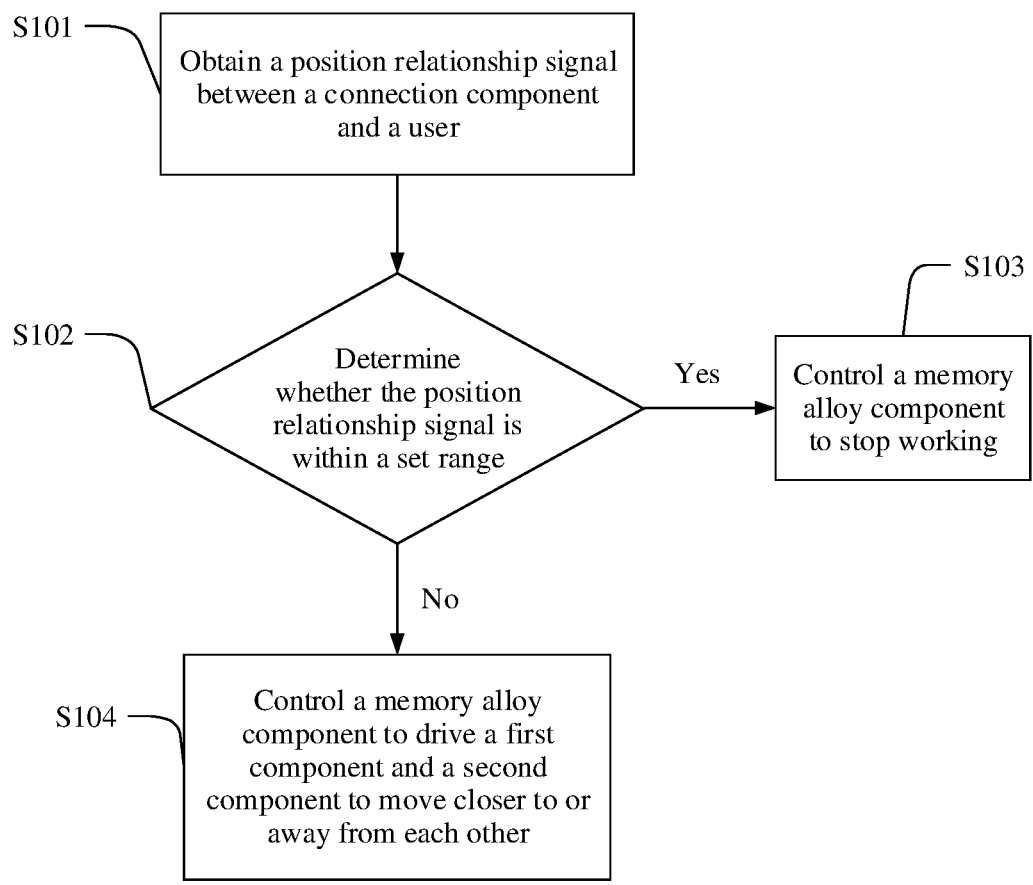
FIG. 20 is a flowchart of a control method of a distance adjustment apparatus according to an embodiment of this application.

Based on a same technical concept, this application further provides a control method of the foregoing specific adjustment apparatus. FIG. 20 is a flowchart of a control method of a distance adjustment apparatus according to an embodiment of this application. Refer to FIG. 20. The foregoing control method includes the following steps.

Step S101: Obtain a position relationship signal between a connection component and a user.

Specifically, a wearable device may include a first sensor, and the first sensor can monitor a position relationship between the wearable device and the user, and generate the position relationship signal. The controller obtains the position relationship signal, to determine, based on the position relationship signal, whether the user is comfortable to wear the wearable device, or whether a working requirement of the wearable device is met.

A type of the first sensor is not limited, and may be at least one type of a force sensor, a capacitive proximity sensor, an ultrasonic distance sensor, a laser ranging sensor, an infrared ranging sensor, and a light sensing sensor. Specifically, the first sensor of a proper type may be selected based on an actual situation. In addition, a quantity of first sensors disposed in the wearable device is not limited, and a large quantity of first sensors may be disposed, to obtain a large quantity of position relationship signals, thereby improving comfort of wearing the wearable device by the user.

Step S102: Determine whether the position relationship signal is within a set range; and if yes, perform step S103, and if no, perform step S104.

Step S103: Control a memory alloy component to stop working.

Step S104: Control the memory alloy component to drive a first component and a second component to move closer to or away from each other.

When the position relationship signal is within the set range, it is considered that a status of the current connection component is proper, and the comfort of wearing the wearable device by the user is high. In this case, the memory alloy component may be controlled to stop working, and the connection component of the wearable device is fixed at this length. When the position relationship signal is outside the set range, it is considered that a status of the current connection component is improper, and the comfort of wearing the wearable device by the user is poor. In this case, the memory alloy component is controlled to drive the first component and the second component to move closer to or away from each other until the position relationship signal detected by the first sensor falls within the set range, so that the user can wear the wearable device comfortably.

In an embodiment, it may be considered that the distance adjustment apparatus is only configured to adjust the connection component to shorten. For example, the distance adjustment apparatus is a watch, and a watchband tends to stretch in a natural state. Therefore, the distance adjustment apparatus is only configured to adjust the connection component to shorten.

In another embodiment, the distance adjustment apparatus may adjust the connection component to shorten, or adjust the connection component to extend. Specifically, in step S102, that the distance adjustment apparatus is controlled to drive the first component and the second component to move closer to or away from each other specifically includes: When the position relationship signal detected by the first sensor is less than the set range, the connection component is excessively long, and the memory alloy component is controlled to drive the first component and the second component to move closer to each other, so that the connection component is shortened. When the position relationship signal detected by the first sensor is greater than the set range, the connection component is excessively short, and the memory alloy component is controlled to drive the first component and the second component to move away from each other, so that the connection component extends. When the position relationship signal detected by the first sensor is within the set range, the length of the connection component is proper, and the memory alloy component is controlled to stop working, so that the connection component is maintained at the current length.

In a specific embodiment, the type of the first sensor is not limited, and a type of the position relationship signal is not limited either. For example, the position relationship signal may be a pressure value or a distance value, or may include both a pressure value and a distance value.

That is, for example, the first sensor is the force sensor, and the position relationship signal is the pressure value. When the pressure value detected by the first sensor is less than the set range, it is considered that the current connection component is excessively long, and the length of the connection component needs to be shortened. In this case, the control memory alloy component drives the first connection component to move closer to the second connection component, so that the length of the connection component is reduced. When the pressure value detected by the first sensor is greater than the set range, it is considered that the current connection component is excessively short, and the length of the connection component needs to be extended. In this case, the distance adjustment apparatus is controlled to drive the first connection component and the second connection component to move away from each other, so that the length of the connection component is increased. When the pressure value detected by the first sensor is within the set range, it is considered that the length of the current connection component is proper. In this case, the memory alloy component is controlled to stop working, so that the connection component is maintained at the current length.

In the foregoing control method, a use state signal of the wearable device is further obtained before step S101. Specifically, the wearable device further includes a second sensor; the second sensor is connected to the controller; the second sensor is configured to send a use state signal to the controller when the wearable device is in a use state; and after obtaining the use state signal, the controller controls power of a current input by a power supply module to the memory alloy component. In this solution, whether the wearable device is currently in the use state may be first determined by using the second sensor. Only when the wearable device is in the use state, the controller controls the memory alloy component of the wearable device to adjust the length of the connection component, to improve reliability of adjusting the length of the connection component by the wearable device.

In addition, the foregoing control method may further include: forming user information through self-learning, and controlling, based on the user information, the memory alloy component to drive the first component and the second component to set positions. In an example in which the wearable device is a headset, head shape feature data of the user may be formed through self-learning, and the length of the connection component is quickly adjusted based on the head shape feature data of the user, to improve a speed at which the user adjusts the length of the connection component of the wearable device.

A specific embodiment is listed below to describe the foregoing control method. In this embodiment, the wearable device is the headset, the connection component is a head beam of the headset, the memory alloy component includes a second return spring and a stop structure, the memory alloy component is a second memory alloy spring, and the second return spring is a second return spring made of a memory alloy. The memory alloy components are disposed on two sides of the head beam and are close to a position of an earmuff. In addition, the head beam of the headset is equipped with the force sensor, which is configured to: sense pressure of a position at which the user wears the headset, and further control the memory alloy component to automatically adjust the length of the connection component. The force sensor is the first sensor. In addition, the headset further includes the second sensor, configured to detect whether the headset is in a wearing state. The second sensor may be a capacitive sensor. A status of whether the headset is worn may be determined by changing a capacitance value of the capacitive sensor in a process of wearing and taking off the headset. Optionally, another sensor such as an optical sensor may be used to perform headset wearing detection.

When the headset is in an initial status, the memory alloy components on the two sides are not powered on, and the stop structure fastens the second memory alloy spring at the top, that is, the head beam is at a highest position. When the second sensor detects that the user wears the headset, the force sensor senses a pressure value between the head of the user and the head beam.

If the pressure value is not within the set range, the second memory alloy spring is enabled. Specifically, when the head beam is initially worn, because the head beam is at the top, the pressure sensor detects a small pressure value, and the second memory alloy spring needs to pull the head beam downwards, that is, shorten the length of the head beam. In this case, the stop structure is controlled to pop up, and the second memory alloy spring is powered on and heated to pull the head beam downwards. A method of starting to heat the second memory alloy spring is to control a circuit by using power management, which includes turning on and off a power supply. In addition, the control circuit may increase instantaneous output power of the circuit by using a power amplification circuit, and improve a heating speed.

The pressure sensor on the head beam continuously senses the pressure value between the head of the user and the head beam, and detects that the pressure value increases and falls within the set range. The second memory alloy spring is controlled to stop working, current power of the second memory alloy spring is powered off or reduced, and the stop structure is controlled to fall, to clamp a current position of the head beam.

If the pressure sensor detects that the pressure value between the head of the user and the head beam is large and exceeds the set range, the second return spring is controlled to push the head beam upwards. Specifically, the stop structure is controlled to pop up, and the head beam is pushed upwards to have the second return spring electrified and heated. A method of starting to heat the second return spring is to control a circuit by using power management, which includes turning on and off a power supply. Optionally, the control circuit may increase instantaneous output power of the circuit by using a power amplification circuit, and improve a heating speed.

The pressure sensor on the head beam continuously senses the pressure value between the head of the user and the head beam, and detects that the pressure value decreases and falls within the set range. The second return spring is controlled to stop working, that is, current power of the second return spring is powered off or reduced, and the stop structure is controlled to fall, to clamp a current position of the head beam.

In addition, when it is detected that the user removes the headset, the stop structure may be further controlled to cancel fastening, and the second return spring may be controlled to push the head beam upwards. After the second return spring extends, the stop structure fastens the head beam at a highest position.

In another embodiment, a control process is similar to the foregoing process. For example, when the first sensor is the distance sensor, the pressure value is replaced with a distance value.

Specifically, when the first sensor is the distance sensor, an example in which the wearable device is the headset is still used. In this embodiment, the connection component is a head beam of the headset, the memory alloy component includes a second return spring and a stop structure, the memory alloy component is a second memory alloy spring, and the second return spring is a second return spring made of a memory alloy. The memory alloy components are disposed on two sides of the head beam and are close to a position of an earmuff. In addition, the head beam of the headset is equipped with the distance sensor, which is configured to: sense a distance between the head beam of the headset and a position at which the user wears the headset, and further control the memory alloy component to automatically adjust the length of the connection component. The distance sensor is the first sensor. In addition, the headset further includes the second sensor, configured to detect whether the headset is in a wearing state. The second sensor may be a capacitive sensor. A status of whether the headset is worn may be determined by changing a capacitance value of the capacitive sensor in a process of wearing and taking off the headset. Optionally, another sensor such as an optical sensor may be used to perform headset wearing detection.

When the headset is in an initial status, the memory alloy components on the two sides are not powered on, and the stop structure fastens the second memory alloy spring at the top, that is, the head beam is at a highest position. When the second sensor detects that the user wears the headset, the distance sensor senses a distance value between the head of the user and the head beam.

If the distance value is not within the set range, the second memory alloy spring is enabled. Specifically, when the head beam is initially worn, because the head beam is at the top, the distance sensor detects a large distance value, and the second memory alloy spring needs to pull the head beam downwards, that is, shorten the length of the head beam. In this case, the stop structure is controlled to pop up, and the second memory alloy spring is powered on and heated to pull the head beam downwards. A method of starting to heat the second memory alloy spring is to control a circuit by using power management, which includes turning on and off a power supply. In addition, the control circuit may increase instantaneous output power of the circuit by using a power amplification circuit, and improve a heating speed.

The distance sensor on the head beam continuously senses the distance value between the head of the user and the head beam, and detects that the distance value decreases and falls within the set range. The second memory alloy spring is controlled to stop working, current power of the second memory alloy spring is powered off or reduced, and the stop structure is controlled to fall, to clamp a current position of the head beam.

If the distance sensor detects that the distance value between the head of the user and the head beam is small and exceeds the set range, the second return spring is controlled to push the head beam upwards. Specifically, the stop structure is controlled to pop up, and the head beam is pushed upwards to have the second return spring electrified and heated. A method of starting to heat the second return spring is to control a circuit by using power management, which includes turning on and off a power supply. Optionally, the control circuit may increase instantaneous output power of the circuit by using a power amplification circuit, and improve a heating speed.

The distance sensor on the head beam continuously senses the distance value between the head of the user and the head beam, and detects that the distance value decreases and falls within the set range. The second return spring is controlled to stop working, that is, current power of the second return spring is powered off or reduced, and the stop structure is controlled to fall, to clamp a current position of the head beam.

In addition, when it is detected that the user removes the headset, the stop structure may be further controlled to cancel fastening, and the second return spring may be controlled to push the head beam upwards. After the second return spring extends, the stop structure fastens the head beam at a highest position.

In addition, the wearable device may further include a plurality of first sensors, and types of the first sensors may be different. For example, the force sensor and the distance sensor may be disposed on the head beam, and the force sensor and the distance sensor are sequentially spaced. The length of the head beam can be adjusted by using the distance sensor, and the length of the head beam can be adjusted by using the force sensor. This helps improve comfort of wearing the wearable device by the user.

Figure 21:
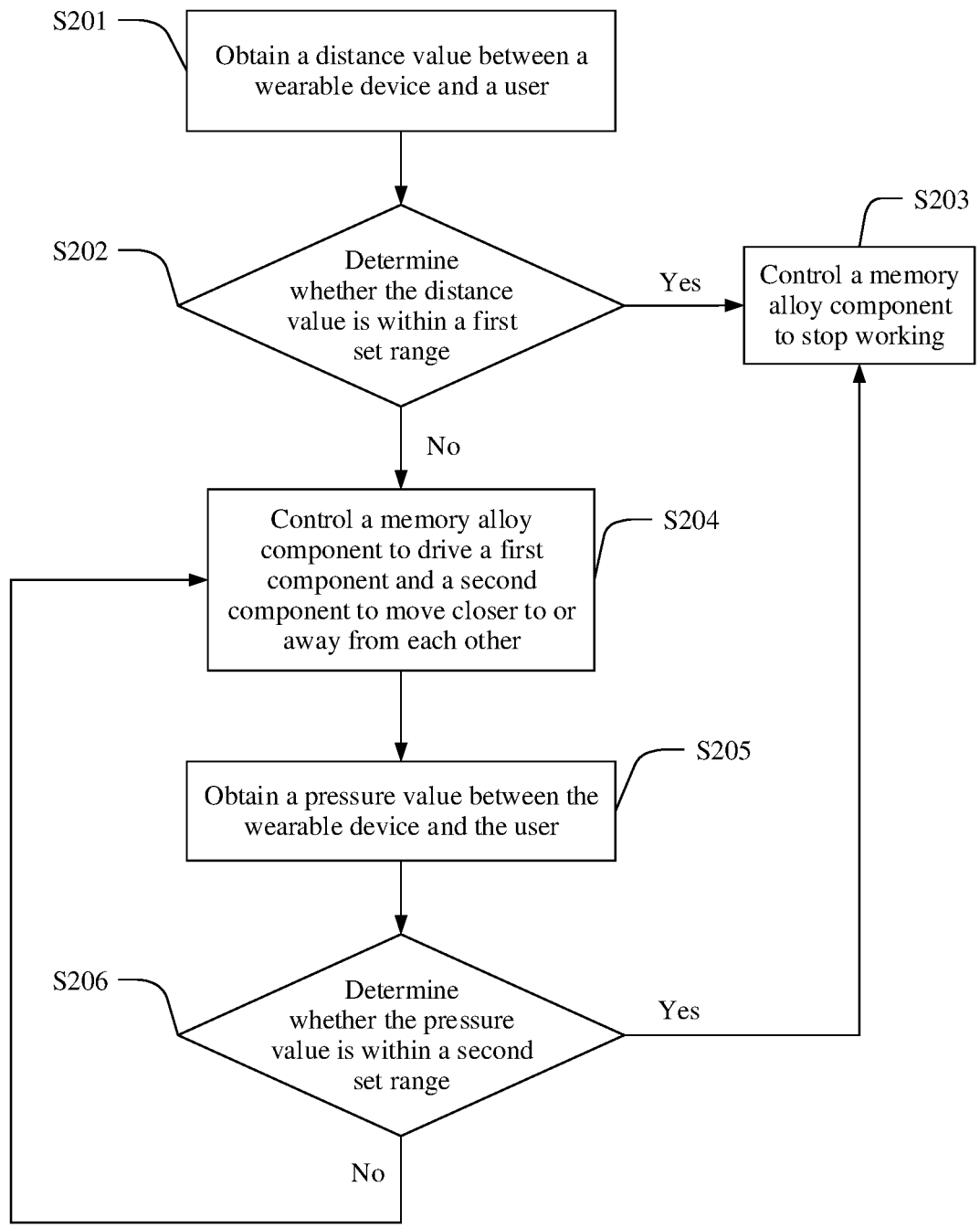
FIG. 21 is a flowchart of a control method of a distance adjustment apparatus according to an embodiment of this application.

FIG. 21 is a flowchart of a control method of a distance adjustment apparatus according to an embodiment of this application. Refer to FIG. 21. The foregoing method includes the following steps.

Step S201: Obtain a distance value between a wearable device and a user.

Step S202: Determine whether a distance value is within a first set range; and if yes, perform step S203, and if no, perform step S204.

Step S203: Control a memory alloy component to stop working.

Step S204: Control the memory alloy component to drive a first component and a second component to move closer to or away from each other.

Step S205: Obtain a pressure value between the wearable device and the user.

Step S206: Determine whether the pressure value is within a second set range; and if yes, perform step S203, and if no, perform step S204.

In a specific embodiment, the wearable device is the headset, the connection component is a head beam of the headset, the memory alloy component includes a second return spring and a stop structure, the memory alloy component is a second memory alloy spring, and the second return spring is a second return spring made of a memory alloy. The memory alloy components are disposed on two sides of the head beam and are close to a position of an earmuff. In addition, the head beam of the headset is equipped with the distance sensor, which is configured to: sense a distance between the head beam of the headset and a position at which the user wears the headset, and further control the memory alloy component to automatically adjust the length of the connection component. The head beam of the headset is also equipped with the force sensor, which is configured to sense pressure between the head beam of the headset and the position at which the user wears the headset. Specifically, the pressure sensor and the distance sensor may be arranged in a staggered manner. In addition, the headset further includes the second sensor, configured to detect whether the headset is in a wearing state. The second sensor may be a capacitive sensor. A status of whether the headset is worn may be determined by changing a capacitance value of the capacitive sensor in a process of wearing and taking off the headset. Optionally, another sensor such as an optical sensor may be used to perform headset wearing detection.

When the headset is in an initial status, the memory alloy components on the two sides are not powered on, and the stop structure fastens the second memory alloy spring at the top, that is, the head beam is at a highest position. When the second sensor detects that the user wears the headset, the distance sensor senses a distance value between the head of the user and the head beam, and the pressure sensor senses a pressure value between the head of the user and the head beam.

If the distance value is not within the first set range, the second memory alloy spring is enabled. Specifically, when the head beam is initially worn, because the head beam is at the top, the distance sensor detects a large distance value, and the second memory alloy spring needs to pull the head beam downwards, that is, shorten the length of the head beam. In this case, the stop structure is controlled to pop up, and the second memory alloy spring is powered on and heated to pull the head beam downwards. A method of starting to heat the second memory alloy spring is to control a circuit by using power management, which includes turning on and off a power supply. In addition, the control circuit may increase instantaneous output power of the circuit by using a power amplification circuit, and improve a heating speed.

The distance sensor on the head beam continuously senses the distance value between the head of the user and the head beam, and detects that the distance value decreases until the distance value falls within the first set range.

If the distance sensor detects that the distance value between the head of the user and the head beam is small and exceeds the first set range, the second return spring is controlled to push the head beam upwards. Specifically, the stop structure is controlled to pop up, and the head beam is pushed upwards to have the second return spring electrified and heated. A method of starting to heat the second return spring is to control a circuit by using power management, which includes turning on and off a power supply. Optionally, the control circuit may increase instantaneous output power of the circuit by using a power amplification circuit, and improve a heating speed.

The distance sensor on the head beam continuously senses the distance value between the head of the user and the head beam, and detects that the distance value decreases until the distance value falls within the first set range.

When the distance value is within the first range, the pressure sensor on the head beam continuously senses the pressure value between the head of the user and the head beam. If the pressure value is not within the second set range, the second memory alloy spring is enabled. The pressure sensor detects a small pressure value, and the second memory alloy spring needs to pull the head beam downwards, that is, shorten the length of the head beam. In this case, the stop structure is controlled to pop up, and the second memory alloy spring is powered on and heated to pull the head beam downwards. A method of starting to heat the second memory alloy spring is to control a circuit by using power management, which includes turning on and off a power supply. In addition, the control circuit may increase instantaneous output power of the circuit by using a power amplification circuit, and improve a heating speed.

The pressure sensor on the head beam continuously senses the pressure value between the head of the user and the head beam, and detects that the pressure value increases and falls within the second set range. The second memory alloy spring is controlled to stop working, current power of the second memory alloy spring is powered off or reduced, and the stop structure is controlled to fall, to clamp a current position of the head beam.

If the pressure sensor detects that the pressure value between the head of the user and the head beam is large and exceeds the second set range, the second return spring is controlled to push the head beam upwards. Specifically, the stop structure is controlled to pop up, and the head beam is pushed upwards to have the second return spring electrified and heated. A method of starting to heat the second return spring is to control a circuit by using power management, which includes turning on and off a power supply. Optionally, the control circuit may increase instantaneous output power of the circuit by using a power amplification circuit, and improve a heating speed.

The pressure sensor on the head beam continuously senses the pressure value between the head of the user and the head beam, and detects that the pressure value decreases and falls within the second set range. The second return spring is controlled to stop working, that is, current power of the second return spring is powered off or reduced, and the stop structure is controlled to fall, to clamp a current position of the head beam.

In addition, when it is detected that the user removes the headset, the stop structure may be further controlled to cancel fastening, and the second return spring may be controlled to push the head beam upwards. After the second return spring extends, the stop structure fastens the head beam at a highest position.

In still another embodiment, self-learning may be further performed in the foregoing control method. In a process in which the user wears the wearable device, user information may be obtained through self-learning. In this way, the user information is formed through self-learning, to understand a wearing habit of the user. The memory alloy component is controlled, based on the user information, to drive the first component and the second component to set positions. In this solution, the length of the connection component of the wearable device can be quickly and accurately adjusted.

It is clear that a person skilled in the art can make various modifications and variations to this application without departing from the scope of this application. This application is intended to cover these modifications and variations of this application provided that they fall within the scope of protection defined by the following claims and their equivalent technologies.

What is claimed is:
1. A distance adjustment apparatus, comprising:
  an auxiliary part;
  a first component and a second component connected to the first component; and
  a memory alloy component disposed in a connection region between the first component and the second component, the memory alloy component configured to drive the first component and the second component closer to or away from each other in response to a current controlling the memory alloy component;

wherein the memory alloy component comprises a first memory alloy component and a second memory alloy component;

wherein the auxiliary part is disposed between the second component and the first component;

wherein when the auxiliary part is in a first status, the first memory alloy component or the second memory alloy component contacts the second component, and when the auxiliary part is in a second status, a gap is disposed between the first memory alloy component and the second component or between the second memory alloy component and the second component;

wherein the first memory alloy component and the second memory alloy component are bent in a first form in a second direction, and are bent in a second form in a first direction;

wherein when the auxiliary part is in the first status, the first memory alloy component changes from the first form to the second form, to drive the second component to move in the first direction, and when the auxiliary part is in the second status, the first memory alloy component changes from the second form to the first form; and wherein when the auxiliary part is in the first status, the second memory alloy component changes from the second form to the first form, to drive the second component to move in the second direction, and when the auxiliary part is in the second status, the second memory alloy component changes from the first form to the second form.

2. The distance adjustment apparatus according to claim 1, wherein:

the first direction is opposite to the second direction;

a first end of the first memory alloy component is fastened to the first component, and a second end of the first memory alloy component drives the second component to move in the first direction relative to the first component;

when a temperature of the first memory alloy component is lower than a set threshold, the first memory alloy component is in the first form;

when the temperature of the first memory alloy component is higher than the set threshold, the first memory alloy component is in the second form;

the first memory alloy component is connected to two electrodes, and the first memory alloy component is configured to change between the first form and the second form in response to a change in the current, to drive the second component to move in the first direction relative to the first component;

a first end of the second memory alloy component is fastened to the first component, and a second end of the second memory alloy component drives the second component to move in a second direction relative to the first component;

when a temperature of the second memory alloy component is lower than a set threshold, the second memory alloy component is in the second form;

when the temperature of the second memory alloy component is higher than the set threshold, the second memory alloy component is in the first form; and the second memory alloy component is connected to two electrodes, and the second memory alloy component is configured to change between the first form and the second form in response to a change in the current, to drive the second component to move in the second direction relative to the first component.

3. The distance adjustment apparatus according to claim 2, further comprising:

a first elastic material layer that is stacked, fastened, and one-to-one corresponds to the first memory alloy component; and a second elastic material layer that is stacked, fastened, and one-to-one corresponds to the second memory alloy component.

4. The distance adjustment apparatus according to claim 2, comprising a plurality of first memory alloy components according to the first memory alloy component and a plurality of second memory alloy components according to the second memory alloy component.

5. The distance adjustment apparatus according to claim 2, wherein the second component is located between the first memory alloy component and the second memory alloy component.

6. The distance adjustment apparatus according to claim 1, wherein:

a first end of the auxiliary part is fastened to the first component, and a second end of the auxiliary part faces the second component;

the first memory alloy component and the second memory alloy component are disposed between the first component and the second component; and when the auxiliary part is in the second status, the second component is driven to move in a direction away from a surface of the first component, a gap is disposed between the second component and the first memory alloy component, the gap is further disposed between the second component and the second memory alloy component.

7. The distance adjustment apparatus according to claim 1, wherein:

the second component is located between the first memory alloy component and the second memory alloy component;

a first end of the auxiliary part is fastened to the first component, the a second end of the auxiliary part faces the second component;

the auxiliary part comprises a first auxiliary part and a second auxiliary part, the first auxiliary part and a first driving part are on a same side, and the second auxiliary part and a second driving part are on a same side;

when the first auxiliary part is in the second status, the second component is driven to move in a direction away from the first driving part, and a gap is disposed between the first driving part and the second component; and when the second auxiliary part is in the second status, the second component is driven to move in a direction away from the second driving part, and a gap is deposed between the first driving part and the second component.

8. The distance adjustment apparatus according to claim 1, wherein:

the auxiliary part comprises a first memory alloy spring, and the first memory alloy spring is connected to two electrodes;

when a temperature of the first memory alloy spring is lower than a set threshold, the first memory alloy spring is of a first length; and when the temperature of the first memory alloy spring is higher than the set threshold, the first memory alloy spring extends towards the second component to a second length and the second component is driven to move away from the first component, wherein the second length is greater than the first length.

9. The distance adjustment apparatus according to claim 8, wherein:
the auxiliary part further comprises a first return spring, the first return spring is disposed in parallel with the first memory alloy spring;
when the first memory alloy spring is of the first length, the first return spring is in an energy release state; and
when the first memory alloy spring is of the second length, the first return spring is in an energy storage state.

10. The distance adjustment apparatus according to claim 1, wherein the first memory alloy component has an elastic layer facing an end of the second component, and the second memory alloy component has an elastic layer facing an end of the second component.

11. The distance adjustment apparatus according to claim 1, wherein:
the first memory alloy component and the second memory alloy component are bent in the first form parallel to the first direction, and are bent in the second form in a direction away from the second component;
the first memory alloy component comprises a first end and a second end that are distributed in the second direction, the first end is fastened to the first component, and the second end is connected to a first linkage rod;
the first linkage rod comprises a third end and a fourth end that are distributed in the second direction, and the second end is rotatably connected to the fourth end;
a first baffle is fastened to the second end of the first memory alloy component, when the first memory alloy component changes from the second form to the first form, the fourth end of the first linkage rod abuts against the first baffle, and the third end of the first linkage rod drives the second component to move in the first direction; and
the second memory alloy component comprises a fifth end and a sixth end that are distributed in the second direction, the sixth end is fastened to the first component, and the fifth end is connected to a second linkage rod;
the second linkage rod comprises a seventh end and an eighth end that are distributed in the second direction, and the fifth end of the second memory alloy component is rotatably connected to the seventh end of the second linkage rod; and
a second baffle is fastened to the fifth end of the second memory alloy component, when the second memory alloy component changes from the second form to the first form, the seventh end of the second linkage rod abuts against the second baffle, and the eighth end of the second linkage rod drives the second component to move in the second direction.

12. The distance adjustment apparatus according to claim 11, wherein the third end of the first linkage rod has an elastic layer, and the eighth end of the second linkage rod has an elastic layer.

13. The distance adjustment apparatus according to claim 1, further comprising a stop structure, wherein the stop structure is disposed between the second component and the first component, when the stop structure is in the first status, the second component moves closer to the first component, and when the stop structure is in the second status, the stop structure is fixedly connected to the second component and the first component.

14. The distance adjustment apparatus according to claim 13, wherein the stop structure comprises a rack, a gear, a clamping member, an elastic member, and a memory alloy structure, wherein the gear is adapted to the rack, and the clamping member is engageable with the gear;
the rack is fixedly disposed in the first component, a rotating shaft of the gear is fixedly disposed in the second component, the elastic member is disposed between the clamping member and the second component, and the memory alloy structure is connected between the clamping member and the second component; or the rack is fixedly disposed in the second component, the rotating shaft of the gear is fixedly disposed in the first component, the elastic member is disposed between the clamping member and the first component, and the memory alloy structure is connected between the clamping member and the first component; and
when a temperature of the memory alloy structure is lower than a set threshold, the memory alloy structure is in the first form, and the elastic member drives the clamping member to engage with the gear; and
when the temperature of the memory alloy structure is higher than the set threshold, the memory alloy structure is in the second form, the clamping member is driven to move away from the gear, the gear moves in mesh with the rack, and the elastic member is in an energy storage state.

15. The distance adjustment apparatus according to claim 1, further comprising:
a second return spring and a stop structure, wherein the memory alloy component is a second memory alloy spring, wherein
a first end of the second memory alloy spring is connected to the first component, a second end of the second memory alloy spring is connected to the second component, and the second memory alloy spring is connected to two electrodes;
when a temperature of the second memory alloy spring is lower than a set threshold, the second memory alloy spring is of a first length;
when the temperature of the second memory alloy spring is higher than the set threshold, the second memory alloy spring telescopically deforms in the first direction to a second length that drives the second component to move in the first direction relative to the first component, wherein the second length is different from the first length;
a first end of the second return spring is connected to the first component, and a second end of the second return spring is connected to the second component; and when the second memory alloy spring is the second length, the second return spring drives the second component to move in the second direction relative to the first component, wherein the first direction is opposite to the second direction; and
the stop structure is disposed between the second component and the first component;
when the stop structure is in a first status, the second component moveable closer to the first component; and
when the stop structure is in a second status, the stop structure is fixedly connected to the second component and the first component.

16. The distance adjustment apparatus according to claim 15, wherein the second return spring is a second return spring made of a memory alloy material.

17. The distance adjustment apparatus according to claim 15, further comprising a first guide member, wherein the first guide member extends in the first direction, and the second return spring and the second memory alloy spring are mounted to the first guide member.

18. The distance adjustment apparatus according to claim 15, wherein a total quantity of second memory alloy springs according to the second memory alloy spring and second return springs according to the second return spring in the distance adjustment apparatus is at least three.

19. The distance adjustment apparatus according to claim 18, wherein:
the second memory alloy springs and the second return springs are spaced one by one; or
the second memory alloy springs are symmetrically arranged about a symmetry axis of the second component, the second return springs are symmetrically arranged about the symmetry axis of the second component, and the symmetry axis extends in the first direction.

20. The distance adjustment apparatus according to claim 15, wherein:
the stop structure comprises a rack, a gear, a clamping member, an elastic member, and a memory alloy structure, wherein the gear is adapted to the rack, and the clamping member can be engaged with the gear;
the rack is fixedly disposed in the first component, a rotating shaft of the gear is fixedly disposed in the second component, the elastic member is disposed between the clamping member and the second component, and the memory alloy structure is connected between the clamping member and the second component; or the rack is fixedly disposed in the second component, the rotating shaft of the gear is fixedly disposed in the first component, the elastic member is disposed between the clamping member and the first component, and the memory alloy structure is connected between the clamping member and the first component;
when a temperature of the memory alloy structure is lower than a set threshold, the memory alloy structure is in a first form, and the elastic member drives the clamping member to engage with the gear; and
when the temperature of the memory alloy structure is higher than the set threshold, the memory alloy structure is in a second form, the clamping member is driven to move away from the gear, the gear moves in mesh with the rack, and the elastic member is in an energy storage state.

* * * * *